US012662513B2

(12) United States Patent
Blackwell et al.

(10) Patent No.: US 12,662,513 B2
(45) Date of Patent: Jun. 23, 2026

(54) **PEPTIDIC MODULATORS OF QUORUM SENSING IN *STAPHYLOCOCCUS EPIDERMIDIS***

(71) Applicant: Wisconsin Alumni Research Foundation, Madison, WI (US)

(72) Inventors: Helen E. Blackwell, Middleton, WI (US); Tian Yang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/098,394

(22) PCT Filed: May 1, 2017

(86) PCT No.: PCT/US2017/030388
§ 371 (c)(1),
(2) Date: Nov. 1, 2018

(87) PCT Pub. No.: WO2017/192442
PCT Pub. Date: Nov. 9, 2017

(65) Prior Publication Data
US 2020/0308230 A1     Oct. 1, 2020

Related U.S. Application Data

(60) Provisional application No. 62/330,211, filed on May 1, 2016.

(51) Int. Cl.
| | |
|---|---|
| *C07K 7/00* | (2006.01) |
| *A61P 31/04* | (2006.01) |
| *C07K 7/56* | (2006.01) |
| *C07K 7/64* | (2006.01) |
| *A61K 38/00* | (2006.01) |

(52) U.S. Cl.
CPC ................ *C07K 7/64* (2013.01); *A61P 31/04* (2018.01); *C07K 7/56* (2013.01); *A61K 38/00* (2013.01)

(58) Field of Classification Search
CPC .. C07K 7/64; C07K 7/56; A61P 31/04; A61K 38/00
See application file for complete search history.

(56) References Cited

U.S. PATENT DOCUMENTS

| | | | |
|---|---|---|---|
| 6,337,385 B1 | 1/2002 | Muir et al. | |
| 6,953,833 B2 | 10/2005 | Muir et al. | |
| 7,419,954 B2 | 9/2008 | Muir et al. | |
| 8,168,397 B2 | 5/2012 | Charlton et al. | |
| 9,227,996 B2 * | 1/2016 | Blackwell | C07K 5/0202 |
| 9,394,371 B2 * | 7/2016 | Janda | A61P 31/04 |
| 2007/0185016 A1 | 8/2007 | Muir et al. | |
| 2014/0256615 A1 | 9/2014 | Blackwell et al. | |
| 2016/0194360 A1 | 7/2016 | Blackwell et al. | |
| 2018/0170889 A1 | 6/2018 | Blackwell et al. | |

FOREIGN PATENT DOCUMENTS

| | | |
|---|---|---|
| WO | 1999/026968 | 6/1999 |
| WO | 2009/154988 | 12/2009 |

OTHER PUBLICATIONS

Search Report and Written Opinion, dated Jan. 23, 2018, corresponding to International Application No. PCT/US2017/030388 (filed May 1, 2017), corresponding to the present application, 13 pp.
Amara et al. (2011) "Macromolecular inhibition of quorum sensing: enzymes, antibodies, and beyond," Chem. Rev. 111:195-208.
Aurelio et al. (2004) "Synthetic preparation of n-methyl alpha amino acids." Chem. Rev. 104: 5823-5846.
Biron et al. (2005) "Convenient Synthesis of N-Methylamino Acids Compatible with Fmoc Solid-Phase Peptide Synthesis," J. Organic Chem. 70:5183-5189.
Boles et al. (2008) "agr-mediated dispersal of *Staphylococcus aureus* biofilms," PLoS Path. 4:e1000052.
Buttner et al. (2015) "Structural basis of *Staphylococcus epidermidis* biofilm formation: mechanisms and molecular interactions," Front. Cell. Infect. Microbiol. 5:14.
Camilli et al. (2006) "Bacterial small-molecule signaling pathways," Science 311:1113-1116.
Carmody et al. (2004) "Specificity grouping of the accessory gene regulator quorum-sensing system of *Staphylococcus epidermidis* is linked to infection," Arch. Microbiol. 181:250-253.
Chan et al. (2004) "Virulence Regulation and Quorum Sensing in Staphylococcal Infections: Competitive AgrC Antagonists as Quorum Sensing Inhibitors," *J. Med. Chem.* 47(19):4633-4641.
Cheung et al. (2014) "Phenol-soluble modulins—critical determinants of staphylococcal virulence," FEMS Microbiol. Rev. 38:698-719.
Claessens et al. (2015) "Inefficacy of vancomycin and teicoplanin in eradicating and killing *Staphylococcus epidermidis* biofilms in vitro," Int. J. Antimicrob. Agents 45:368-375.
Costerton et al. (1999) "Bacterial biofilms: a common cause of persistent infections," Science 284:1318-1322.

(Continued)

*Primary Examiner* — Jeanette M Lieb
(74) *Attorney, Agent, or Firm* — Leydig, Voit & Mayer, Ltd.

(57) ABSTRACT

Synthetic cyclic peptide modulators of the AgrC quorum sensing system of *S. epidermidis*. Synthetic agonists and antagonist of AgrC-I are described. Compounds capable of either pan-group or group-selective AgrC receptor inhibition in *S. epidermidis* were identified. Additionally, compounds that are species selective, and could be applied to selectively modulate either *S. epidermidis* or *S. aureus* AgrC receptors were identified. An AgrC-I agonist was found which strongly inhibits *S. epidermidis* biofilm growth, with a higher potency and efficacy than that of native AIP-I. Methods of modulating virulence in *S. epidermidis* and related *Staphylococcus* by contacting a bacterium or a bacterial environment, such as a biofilm, with a modulator of the disclosure are provided. Methods are provided for treating infections of *S. epidermidis* and related *Staphylococcus* by administering a therapeutically effective amount of one or more compounds herein to an individual in need thereof.

5 Claims, 13 Drawing Sheets

Specification includes a Sequence Listing.

(56)  References Cited

OTHER PUBLICATIONS

Doneux et al. (2010) "Influence of the Interfacial Peptide Organization on the Catalysis of Hydrogen Evolution," Langmuir 26(2):1347-1353.

Fleming et al. (2006) "Agr interference between clinical *Staphylococcus aureus* strains in an insect model of virulence," J. Bacteriol. 188:7686-7688.

Fowler et al. (2008) "Design and synthesis of macrocyclic peptomers as mimics of a quorum sensing signal from *Staphylococcus aureus*," Org. Lett. 10:2329-2332.

George et al. (2008) "Cyclic peptide inhibitors of staphylococcal virulence prepared by Fmoc-based thiolactone peptide synthesis," J. Am. Chem. Soc. 130:4914-4924.

George Cisar et al. (2009) "Symmetric signalling within asymmetric dimers of the *Staphylococcus aureus* receptor histidine kinase AgrC," Mol. Microbiol. 74:44-57.

George et al. (2007) "Molecular mechanisms of agr quorum sensing in virulent staphylococci," ChemBioChem 8:847-855.

Gorske et al. (2006) "Interception of Quorum Sensing in *Staphylococcus aureus*: A New Niche for Peptidomimetics," Org. Biomol. Chem. 4:1441-1445.

Hellmark et al. (2013) "Comparison of *Staphylococcus epidermidis* isolated from prosthetic joint infections and commensal isolates in regard to antibiotic susceptibility, agr type, biofilm production, and epidemiology," Int. J. Med. Microbiol. 303:32-39.

Jarraud et al. (2000) "Exfoliatin-Producing Strains Define a Fourth agr Specificity Group in *Staphylococcus aureus*," *J. Bacteriol.* 182(22):6517-6522.

Ji et al. (1995) "Cell density control of staphylococcal virulence mediated by an octapeptide pheromone," Proc. Natl. Acad. Sci. USA 92:12055-12059.

Ji et al. (1997) "Bacterial interference caused by autoinducing peptide variants," Science 276:2027-2030.

Johnson et al. (2015) "Increasing AIP Macrocycle Size Reveals Key Features of agr Activation in *Staphylococcus aureus*," ChemBioChem 16:1093-1100.

Kaufmann et al. (2008) "Bacterial Quorum Sensing: A New Target for Anti-Infective Immunotherapy," *Exp. Opin. Biol. Ther.* 8(6)719-724.

Kavanaugh et al. (2007) "A role for type I signal peptidase in *Staphylococcus aureus* quorum sensing," Mol. Microbiol. 65:780-798.

Khan et al. (2015) "Investigational therapies targeting quorum-sensing for the treatment of *Staphylococcus aureus* infections," Expert Opin. Investig. Drugs 24:689-704.

Kirchdoerfer et al. (2011) "Structural basis for ligand recognition and discrimination of a quorum-quenching antibody," J. Biol. Chem. 286:17351-17358.

Klug et al. (2003) "Involvement of adherence and adhesion *Staphylococcus epidermidis* genes in pacemaker lead-associated infections," J. Clin. Microbiol. 41:3348-3350.

Kong et al. (2006) "*Staphylococcus* quorum sensing in biofilm formation and infection," Int. J. Med. Microbiol. 296:133-139.

Kotelchuck et al. (1972) "Conformational Energy Studies of Oxytocin and Its Cyclic Moiety," Proc Natl Acad Sci USA 69(12):3629-3633.

Le et al. (2014) "Molecular determinants of staphylococcal biofilm dispersal and structuring," Front. Cell. Infect. Microbiol. 4:167, 7 pp.

Lianhua et al. (2014) "The effect of iatrogenic *Staphylococcus epidermidis* intercellar adhesion operon on the formation of bacterial biofilm on polyvinyl chloride surfaces," Surg. Infect. (Larchmt) 15:768-773.

Li et al. (2011) "*Lactobacillus reuteri*-Produced Cyclic Dipeptides Quench agr-Mediated Expression of Toxic Shock Syndrome Toxin-1 in Staphylococci," *Proc. Natl. Acad. Sci. U.S. A.* 2011, 108:3360-3365.

Lina et al. (2003) "Bacterial Competition for Human Nasal Cavity Colonization: Role of Staphylococcal agr Alleles," Appl. Environ. Microbiol. 69:18-23.

Lyon et al. (2004) "Peptide signaling in *Staphylococcus aureus* and other Gram-positive bacteria," Peptides 25:1389-1403.

Lyon et al. (2000) "Rational design of a global inhibitor of the virulence response in *Staphylococcus aureus*, based in part on localization of the site of inhibition to the receptor-histidine kinase, AgrC," Proc. Natl. Acad. Sci. USA 97:13330-13335.

Lyon et al. (2002) "Key determinants of receptor activation in the agr autoinducing peptides of *Staphylococcus aureus*," Biochemistry 41:10095-10104.

Lyon et al. (2002) "Reversible and Specific Extracellular Antagonism of Receptor-Histidine Kinase Signaling". J. Biol. Chem. 277:6247-6253.

Mack et al. (2007) "Microbial interactions in *Staphylococcus epidermidis* biofilms," Anal. Bioanal. Chem. 387:399-408.

Malone et al. (2007) "Biosynthesis of *Staphylococcus aureus* Autoinducing Peptides by Using the Synechocystis DnaB Mini-intein," *Appl. Environ. Microbiol.* 73:6036-6044.

Mayville et al. (1999) "Structure-activity analysis of synthetic autoinducing thiolactone peptides from *Staphylococcus aureus* responsible for virulence," Proc. Natl. Acad. Sci. USA 96:1218-1223.

Mccann et al. (2008) "*Staphylococcus epidermidis* device-related infections: pathogenesis and clinical management," J. Pharm. Pharmacol. 60:1551-1571.

Mcdowell et al. (2001) "Structure, activity and evolution of the group I thiolactone peptide quorum-sensing system of *Staphylococcus aureus*," Mol. Microbiol. 41:503-512.

Mertens et al. (2013) "Genetic determinants and biofilm formation of clinical *Staphylococcus epidermidis* isolates from blood cultures and indwelling devises," Eur. J. Microbiol. Immunol. (Bp) 3:111-119.

Novick et al. (2008) "Quorum sensing in staphylococci," Annu. Rev. Genet. 42:541-564.

Novick et al. (1993) "Synthesis of staphylococcal virulence factors is controlled by a regulatory RNA molecule," EMBO J. 12:3967-3975.

Olson et al. (2014) "*Staphylococcus epidermidis* agr quorum-sensing system: signal identification, cross talk, and importance in colonization," J. Bacteriol. 196:3482-3493.

Otto et al. (1998) "Structure of the pheromone peptide of the *Staphylococcus epidermidis* agr system," FEBS Lett. 424:89-94.

Otto et al. (1999) "Inhibition of virulence factor expression in *Staphylococcus aureus* by the *Staphylococcus epidermidis* agr pheromone and derivatives," FEBS Lett. 450:257-262.

Otto et al. (2001) "Pheromone cross-inhibition between *Staphylococcus aureus* and *Staphylococcus epidermidis*," Infect. Immun. 69:1957-1960.

Otto, M. (2001) "*Staphylococcus aureus* and *Staphylococcus epidermidis* peptide pheromones produced by the accessory gene regulator agr system," Peptides 22:1603-1608.

Otto, M. (2004) "Quorum-sensing control in Staphylococci—a target for antimicrobial drug therapy?," FEMS Microbiol. Lett. 241:135-141.

Otto, M. (2004) "Virulence factors of the coagulase-negative staphylococci," Front. Biosci. 9:841-863.

Otto, M. (2009) "*Staphylococcus epidermidis*—the 'accidental' pathogen," Nat. Rev. Microbiol. 7:555-567.

Otto, M. (2013) "Staphylococcal infections: mechanisms of biofilm maturation and detachment as critical determinants of pathogenicity," Annu. Rev. Med. 64:175-188.

Otto, M. (2014) "Phenol-soluble modulins," Int. J. Med. Microbiol. 304:164-169.

Praneenararat et al. (2012) "Chemical methods to interrogate bacterial quorum sensing pathways," Org. Biomol. Chem. 10:8189-8199.

Rasko et al. (2010) "Anti-virulence strategies to combat bacteria-mediated disease," *Nat. Rev. Drug Disc.* 9(2):117-128.

Rogers et al. (2009) "Coagulase-negative staphylococcal infections," Infect. Dis. Clin. North Am. 23:73-98.

Rutherford et al. (2012) "Bacterial quorum sensing: its role in virulence and possibilities for its control," Cold Spring Harb. Perspect. Med. 2, a012427.

(56) References Cited

OTHER PUBLICATIONS

Schaeffer et al. (2015) "Accumulation-associated protein enhances *Staphylococcus epidermidis* biofilm formation under dynamic conditions and is required for infection in a rat catheter model," Infect. Immun. 83:214-226.

Scott et al. (2003) "Side-chain-to-tail thiolactone peptide inhibitors of the staphylococcal quorum-sensing system," Bioorg. Med. Chem. Lett. 13:2449-2453.

Sintim et al. (2010) "Paradigm Shift in Discovering Next-Generation Anti-Infective Agents: Targeting Quorum Sensing, c-di-GMP Signaling and Biofilm in Bacteria with Small Molecules," Future Med. Chem. 2010, 2:1005-1035.

Stacy (Apr. 6, 2012) "Attenuation of Quorum Sensing and Virulence in the Pathogen *Staphylococcus aureus* Using Synthetic Autoinducer Mimics," In; The Lincoln Seminar Series. The University of Wisconsin-Madison. Madison, Wisconsin.

Stacy et al. (Apr. 13, 2012) "Attenuation of Quorum Sensing and Virulence in the Pathogen *Staphylococcus aureus* Using Synthetic Autoinducer Mimics," In; Perlman Symposium on Antibiotic Discovery and Development. Madison, Wisconsin.

Tal-Gan et al. (Aug. 7-8, 2008) "The Application of Peptidomimetics to Study Quorum Sensing in *Staphylococcus aureus*," In; The 6th Peptoid Summit. Berkeley, California.

Tal-Gan et al. (Feb. 18-19, 2012) "Development of Peptide-Based Tools to Study Quorum Sensing in *Staphylococcus aureus*," In; Gordon Research Conference: Peptides, Chemistry and Biology of (GRS). Ventura, California.

Tal-Gan et al. (2013) "Structural characterization of native autoinducing peptides and abiotic analogues reveals key features essential for activation and inhibition of an AgrC quorum sensing receptor in *Staphylococcus aureus*," J. Am. Chem. Soc. 135:18436-18444.

Tal-Gan et al. (2013) "Highly potent inhibitors of quorum sensing in *Staphylococcus aureus* revealed through a systematic synthetic study of the group-III autoinducing peptide," J. Am. Chem. Soc. 135:7869-7882.

Tal-Gan et al. (2014) "N-Methyl and peptoid scans of an autoinducing peptide reveal new structural features required for inhibition and activation of AgrC quorum sensing receptors in *Staphylococcus aureus*," Chem. Commun. (Camb.) 50:3000-3003.

Tal-Gan et al. (Jan. 2016) "Characterization of Structural Elements in Native Autoinducing Peptides and Non-Native Analogues that Permit the Differential Modulation of AgrC-type Quorum Sensing Receptors in *Staphylococcus aureus*". Org Biomol. Chem. 14:113-121.

Tal-Gan et al. (Jul. 2016) "Highly Stable, Amide-Bridged Autoinducing Peptide Analogues that Strongly Inhibit the AgrC Quorum Sensing Receptor in *Staphylococcus aureus*". Angew Chem. Int. Ed Engl. 55: 8913-8917.

Thoendel et al. (2011) "Peptide signaling in the staphylococci," *Chem. Rev.* 111, 117-151.

Vasquez et al. (Feb. 2017) "Simplified AIP-II Peptidomimetics are Potent Inhibitors of *Staphylococcus aureus* AgrC Quorum Sensing Receptors". ChemBioChem. 18:413-423.

Von Eiff et al. (2002) "Pathogenesis of infections due to coagulase-negative staphylococci," Lancet Infect. Dis. 2:677-685.

Vuong et al. (2004) "Regulated expression of pathogen-associated molecular pattern molecules in *Staphylococcus epidermidis*: quorum-sensing determines pro-inflammatory capacity and production of phenol-soluble modulins," Cell. Microbiol. 6:753-759.

Vuong et al. (2002) "*Staphylococcus epidermidis* infections," Microb. Infect. 4:481-489.

Vuong et al. (2003) "Quorum-sensing control of biofilm factors in *Staphylococcus epidermidis*," J. Infect. Dis. 188:706-718.

Vuong et al. (2004) "Increased colonization of indwelling medical devices by quorum-sensing mutants of *Staphylococcus epidermidis* in vivo," J. Infect. Dis. 190:1498-1505.

Wang et al. (2007) "Role of ClpP in biofilm formation and virulence of *Staphylococcus epidermidis*," Microb. Infect. 9:1376-1383.

Wang et al. (2014) "Activation and inhibition of the receptor histidine kinase AgrC occurs through opposite helical transduction motions," Mol. Cell 53:929-940.

Wang et al. (2011) "*Staphylococcus epidermidis* surfactant peptides promote biofilm maturation and dissemination of biofilm-associated infection in mice," J. Clin. Invest. 121:238-248.

Wang et al. (Feb. 2016) "Regulation of virulence in *Staphylococcus aureus*: molecular mechanisms and remaining puzzles". Cell Chem. Biol. 23:214-224.

Wright et al. (2004) "Hydrophobic Interactions Drive Ligand-Receptor Recognition for Activation and Inhibition of Staphylococcal Quorum Sensing," *Proc. Natl. Acad. Sci. U. S. A.* 101(46):16168-16173.

Wright et al. (2005) "Transient interference with staphylococcal quorum sensing blocks abscess formation," Proc. Natl. Acad. Sci. USA 102:1691-1696.

Yang et al. (Jul. 2016) "Structure-Function Analyses of a *Staphylococcus epidermidis* Autoinducing Peptide Reveals Motifs Critical for AgrC-type Receptor Modulation". ACS Chem. Biol. 11(7):1982-1991.

Yao et al. (2006) "Characterization of the *Staphylococcus epidermidis* accessory-gene regulator response: quorum-sensing regulation of resistance to human innate host defense," J. Infect. Dis. 193:841-848.

U.S. Appl. No. 13/792,977, filed May 11, 2013, Abandoned.

U.S. Appl. No. 14/109,193, filed Dec. 17, 2013, Granted, 2014/0256615 A1, U.S. Pat. No. 9,227,996, Jan. 5, 2016.

U.S. Appl. No. 14/987,457, filed Jan. 4, 2016, Pending, 2016/0194360 A1.

U.S. Appl. No. 15/850,300, filed Dec. 21, 2017, Pending, US-2018-0170889.

* cited by examiner

S. epidermidis AIP-I

S. epidermidis AIP-II

S. epidermidis AIP-III

SEQUENCE LISTING

```
<160> NUMBER OF SEQ ID NOS: 184

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Tyr Leu Pro Cys Ser Asn Tyr Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Tyr Val Pro Cys Ser Asn Tyr Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 3

Lys Tyr Asn Val Cys Ser Asn Tyr Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 4

Lys Tyr Asn Val Cys Ala Asn Tyr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 5

Lys Tyr Asn Val Cys Ser Ala Tyr Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 6

Lys Tyr Asn Val Cys Ser Ser Tyr Leu
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MISC_FEATURE
<222> LOCATION: (3)..(7)
<223> OTHER INFORMATION: Cyclic

<400> SEQUENCE: 7

Ile Asn Cys Ala Phe Leu Leu
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MISC_FEATURE
<222> LOCATION: (4)..(8)
<223> OTHER INFORMATION: Cyclic
```

```
<400> SEQUENCE: 8

Tyr Ser Thr Cys Asp Phe Ile Met
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 9

Gly Val Asn Ala Cys Ser Ser Leu Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(7)
<223> OTHER INFORMATION: Cyclic

<400> SEQUENCE: 10

Ile Asn Cys Asp Phe Leu Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 11

Tyr Ser Thr Cys Tyr Phe Ile Met
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 12

Cys Ser Asn Tyr Leu
1               5
```

```
<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 13

Xaa Ser Asn Tyr Leu
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 14

Cys Ala Ala Tyr Phe
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 15

Xaa Ala Ala Tyr Phe
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 16

Cys Ser Ala Tyr Phe
1               5
```

-continued

```
<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 17

Xaa Ser Ala Tyr Phe
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 18

Cys Ala Asn Tyr Leu
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 19

Cys Ala Asn Tyr Phe
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 20

Cys Ala Asn Leu Phe
1               5

<210> SEQ ID NO 21
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 21

Cys Ala Asn Phe Leu
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 22

Cys Ser Ser Tyr Leu
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 23

Cys Ser Ser Tyr Phe
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 24

Cys Ser Ser Leu Phe
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
```

```
<222> LOCATION: (1)..(5)
<223> OTHER INFORMATION: Cyclic

<400> SEQUENCE: 25

Cys Ser Ser Phe Leu
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 26

Cys Ala Ser Tyr Leu
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 27

Cys Ala Ser Tyr Phe
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 28

Cys Ala Ser Leu Phe
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 29

Cys Ala Ser Phe Leu
1               5
```

```
<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 30

Cys Ser Ala Tyr Leu
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 31

Cys Ser Ala Leu Phe
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 32

Cys Ser Ala Phe Leu
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 33

Cys Ala Ala Tyr Leu
1               5

<210> SEQ ID NO 34
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 34

Cys Ala Ala Leu Phe
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 35

Cys Ala Ala Phe Leu
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 36

Cys Tyr Ser Tyr Leu
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 37

Cys Tyr Ser Tyr Phe
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic
```

```
<400> SEQUENCE: 38

Cys Tyr Ser Leu Phe
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 39

Cys Tyr Ser Phe Leu
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 40

Cys Ser Asn Tyr Phe
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 41

Cys Ser Asn Leu Phe
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclic

<400> SEQUENCE: 42

Cys Ser Asn Phe Leu
1               5

<210> SEQ ID NO 43
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 43

Xaa Ala Asn Tyr Leu
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 44

Xaa Ala Asn Tyr Phe
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 45

Xaa Ala Asn Leu Phe
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
```

```
<223> OTHER INFORMATION: Cyclic

<400> SEQUENCE: 46

Xaa Ala Asn Phe Leu
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 47

Xaa Ser Ser Tyr Leu
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 48

Xaa Ser Ser Tyr Phe
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 49

Xaa Ser Ser Leu Phe
1               5

<210> SEQ ID NO 50
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 50

Xaa Ser Ser Phe Leu
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 51

Xaa Ala Ser Tyr Leu
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 52

Xaa Ala Ser Tyr Phe
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 53
```

```
Xaa Ala Ser Leu Phe
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 54

Xaa Ala Ser Phe Leu
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 55

Xaa Ser Ala Tyr Leu
1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 56

Xaa Ser Ala Leu Phe
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

-continued

```
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 57

Xaa Ser Ala Phe Leu
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 58

Xaa Ala Ala Tyr Leu
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 59

Xaa Ala Ala Leu Phe
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 60

Xaa Ala Ala Phe Leu
1               5
```

```
<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 61

Xaa Tyr Ser Tyr Leu
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 62

Xaa Tyr Ser Tyr Phe
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 63

Xaa Tyr Ser Leu Phe
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
```

```
<222> LOCATION: (1)..(5)
<223> OTHER INFORMATION: Cyclic

<400> SEQUENCE: 64

Xaa Tyr Ser Phe Leu
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 65

Xaa Ser Asn Tyr Phe
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 66

Xaa Ser Asn Leu Phe
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MISC_FEATURE
<222> LOCATION: (1)..(5)
<223> OTHER INFORMATION: Cyclic

<400> SEQUENCE: 67

Xaa Ser Asn Phe Leu
1               5

<210> SEQ ID NO 68
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 68

Asp Ser Val Cys Ala Ser Tyr Phe
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 69

Ala Ser Val Cys Ala Ala Tyr Phe
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 70

Ala Ser Ile Cys Ala Ala Tyr Phe
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 71

Ala Ser Leu Cys Ala Ala Tyr Phe
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic
```

<400> SEQUENCE: 72

Ala Ser Val Cys Ala Ser Tyr Phe
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 73

Ala Ser Val Xaa Ala Ala Tyr Phe
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 74

Ala Ser Ile Xaa Ala Ala Tyr Phe
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 75

Ala Ser Leu Xaa Ala Ala Tyr Phe
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 76

Ala Ser Val Xaa Ala Ser Tyr Phe
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 77

Asp Ser Val Cys Ala Ala Tyr Phe
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 78

Asp Ser Val Xaa Ala Ala Tyr Phe
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 79

Asp Ser Val Xaa Ala Ser Tyr Phe
1               5

<210> SEQ ID NO 80
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (8)..(12)
<223> OTHER INFORMATION: Cyclic

<400> SEQUENCE: 80

Asn Ala Ser Lys Tyr Asn Pro Cys Ala Ser Tyr Leu
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Dab
<220> FEATURE:
<221> NAME/KEY: MISC_FEATURE
<222> LOCATION: (8)..(12)
<223> OTHER INFORMATION: Cyclic

<400> SEQUENCE: 81

Asn Ala Ser Lys Tyr Asn Pro Xaa Ala Ser Tyr Leu
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (8)..(12)
<223> OTHER INFORMATION: Cyclic

<400> SEQUENCE: 82

Asn Ala Ala Lys Tyr Asn Pro Cys Ser Asn Tyr Leu
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Dab
<220> FEATURE:
<221> NAME/KEY: MISC_FEATURE
<222> LOCATION: (8)..(12)
<223> OTHER INFORMATION: Cyclic

<400> SEQUENCE: 83

Asn Ala Ala Lys Tyr Asn Pro Xaa Ser Asn Tyr Leu
1               5                   10
```

-continued

```
<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 84

Asp Ser Val Cys Tyr Ser Tyr Phe
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 85

Asp Ser Val Cys Ser Ser Tyr Phe
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 86

Asp Ser Ala Cys Tyr Ser Tyr Phe
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 87

Asp Ser Ala Cys Ser Ser Tyr Phe
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MISC_FEATURE
<222> LOCATION: (4)..(8)
<223> OTHER INFORMATION: Cyclic

<400> SEQUENCE: 88

Asp Ser Ala Cys Ser Asn Tyr Leu
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 89

Asp Ser Ala Cys Ala Ala Tyr Phe
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 90

Asp Ser Ala Cys Ser Ala Tyr Phe
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 91

Ala Ser Ala Cys Tyr Ser Tyr Phe
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 92
```

Ala Ser Ala Cys Ser Ser Tyr Phe
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 93

Ala Ser Ala Cys Ser Asn Tyr Leu
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 94

Ala Ser Ala Cys Ala Ala Tyr Phe
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 95

Ala Ser Ala Cys Ser Ala Tyr Phe
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 96

Lys Tyr Asn Pro Cys Tyr Ser Tyr Phe
1               5

```
<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 97

Lys Tyr Asn Pro Cys Ser Ser Tyr Phe
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 98

Lys Tyr Asn Pro Cys Ser Asn Tyr Leu
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 99

Lys Tyr Asn Pro Cys Ala Ala Tyr Phe
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
```

-continued

```
<221> NAME/KEY: MISC_FEATURE
<222> LOCATION: (5)..(9)
<223> OTHER INFORMATION: Cyclic

<400> SEQUENCE: 100

Lys Tyr Asn Pro Cys Ser Ala Tyr Phe
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 101

Asp Ser Val Xaa Tyr Ser Tyr Phe
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 102

Asp Ser Val Xaa Ser Ser Tyr Phe
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 103

Asp Ser Ala Xaa Tyr Ser Tyr Phe
1               5

<210> SEQ ID NO 104
<211> LENGTH: 8
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 104

Asp Ser Ala Xaa Ser Ser Tyr Phe
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 105

Asp Ser Ala Xaa Ser Asn Tyr Leu
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 106

Asp Ser Ala Xaa Ala Ala Tyr Phe
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic
```

```
<400> SEQUENCE: 107

Asp Ser Ala Xaa Ser Ala Tyr Phe
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 108

Ala Ser Ala Xaa Tyr Ser Tyr Phe
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 109

Ala Ser Ala Xaa Ser Ser Tyr Phe
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 110

Ala Ser Ala Xaa Ser Asn Tyr Leu
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 111

Ala Ser Ala Xaa Ala Ala Tyr Phe
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab
<220> FEATURE:
<221> NAME/KEY: MISC_FEATURE
<222> LOCATION: (4)..(8)
<223> OTHER INFORMATION: Cyclic

<400> SEQUENCE: 112

Ala Ser Ala Xaa Ser Ala Tyr Phe
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dab
<220> FEATURE:
<221> NAME/KEY: MISC_FEATURE
<222> LOCATION: (5)..(9)
<223> OTHER INFORMATION: Cyclic

<400> SEQUENCE: 113

Lys Tyr Asn Pro Xaa Tyr Ser Tyr Phe
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dab
<220> FEATURE:
```

```
<221> NAME/KEY: MISC_FEATURE
<222> LOCATION: (5)..(9)
<223> OTHER INFORMATION: Cyclic

<400> SEQUENCE: 114

Lys Tyr Asn Pro Xaa Ser Ser Tyr Phe
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dab
<220> FEATURE:
<221> NAME/KEY: MISC_FEATURE
<222> LOCATION: (5)..(9)
<223> OTHER INFORMATION: Cyclic

<400> SEQUENCE: 115

Lys Tyr Asn Pro Xaa Ser Asn Tyr Leu
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dab
<220> FEATURE:
<221> NAME/KEY: MISC_FEATURE
<222> LOCATION: (5)..(9)
<223> OTHER INFORMATION: Cyclic

<400> SEQUENCE: 116

Lys Tyr Asn Pro Xaa Ala Ala Tyr Phe
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dab
<220> FEATURE:
<221> NAME/KEY: MISC_FEATURE
```

-continued

```
<222> LOCATION: (5)..(9)
<223> OTHER INFORMATION: Cyclic

<400> SEQUENCE: 117

Lys Tyr Asn Pro Xaa Ser Ala Tyr Phe
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 118

Gly Val Asn Ala Cys Ser Asn Tyr Leu
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 119

Gly Val Asn Ala Cys Ala Ala Tyr Phe
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 120

Gly Val Asn Ala Cys Ser Ala Tyr Phe
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Dab
<220> FEATURE:
<221> NAME/KEY: MISC_FEATURE
<222> LOCATION: (5)..(9)
<223> OTHER INFORMATION: Cyclic
```

-continued

```
<400> SEQUENCE: 121

Gly Val Asn Ala Xaa Ser Asn Tyr Leu
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Dab
<220> FEATURE:
<221> NAME/KEY: MISC_FEATURE
<222> LOCATION: (5)..(9)
<223> OTHER INFORMATION: Cyclic

<400> SEQUENCE: 122

Gly Val Asn Ala Xaa Ala Ala Tyr Phe
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Dab
<220> FEATURE:
<221> NAME/KEY: MISC_FEATURE
<222> LOCATION: (5)..(9)
<223> OTHER INFORMATION: Cyclic

<400> SEQUENCE: 123

Gly Val Asn Ala Xaa Ser Ala Tyr Phe
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (3)..(3)
<223> OTHER INFORMATION: Asn, Leu or Val
<220> FEATURE:
<221> NAME/KEY: MOD_RES
<222> LOCATION: (5)..(5)
<223> OTHER INFORMATION: Cys or Dab
<220> FEATURE:
<221> NAME/KEY: MISC_FEATURE
<222> LOCATION: (5)..(9)
<223> OTHER INFORMATION: Cyclic
<220> FEATURE:
<221> NAME/KEY: MOD_RES
<222> LOCATION: (6)..(6)
<223> OTHER INFORMATION: Ala or Ser
<220> FEATURE:
<221> NAME/KEY: MOD_RES
```

<222> LOCATION: (7)..(7)
<223> OTHER INFORMATION: Asn or Ser

<400> SEQUENCE: 124

Lys Tyr Xaa Pro Xaa Xaa Xaa Tyr Leu
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 125

Lys Tyr Asn Pro Cys Ala Ser Tyr Leu
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 126

Lys Tyr Asn Pro Cys Ala Asn Tyr Leu
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 127

Lys Tyr Asn Pro Cys Ser Ser Tyr Leu
1               5

<210> SEQ ID NO 128
<211> LENGTH: 9
<212> TYPE: PRT
<213> ORGANISM: Artificial Sequence -continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 128

Lys Tyr Leu Pro Cys Ala Ser Tyr Leu
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 129

Lys Tyr Leu Pro Cys Ala Asn Tyr Leu
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 130

Lys Tyr Leu Pro Cys Ser Ser Tyr Leu
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 131
```

```
Lys Tyr Asn Val Cys Ala Ser Tyr Leu
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 132

Lys Tyr Asn Val Cys Ala Asn Tyr Leu
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 133

Lys Tyr Asn Val Cys Ser Ser Tyr Leu
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 134

Lys Tyr Val Pro Cys Ala Ser Tyr Leu
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 135

Lys Tyr Val Pro Cys Ala Asn Tyr Leu
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 136

Lys Tyr Val Pro Cys Ser Ser Tyr Leu
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 137

Lys Tyr Leu Pro Cys Ser Asn Tyr Leu
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 138

Lys Tyr Asn Val Cys Ser Asn Tyr Leu
1               5
```

-continued

```
<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MISC_FEATURE
<222> LOCATION: (5)..(9)
<223> OTHER INFORMATION: Cyclic

<400> SEQUENCE: 139

Lys Tyr Val Pro Cys Ser Asn Tyr Leu
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 140

Lys Tyr Asn Pro Xaa Ala Ser Tyr Leu
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 141

Lys Tyr Asn Pro Xaa Ala Asn Tyr Leu
1               5

<210> SEQ ID NO 142
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 142

Lys Tyr Asn Pro Xaa Ser Ser Tyr Leu
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 143

Lys Tyr Leu Pro Xaa Ala Ser Tyr Leu
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 144

Lys Tyr Leu Pro Xaa Ala Asn Tyr Leu
1               5

<210> SEQ ID NO 145
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 145

Lys Tyr Leu Pro Xaa Ser Ser Tyr Leu
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 146

Lys Tyr Asn Val Xaa Ala Ser Tyr Leu
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 147

Lys Tyr Asn Val Xaa Ala Asn Tyr Leu
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 148

Lys Tyr Asn Val Xaa Ser Ser Tyr Leu
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 149

Lys Tyr Val Pro Xaa Ala Ser Tyr Leu
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 150

Lys Tyr Val Pro Xaa Ala Asn Tyr Leu
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 151

Lys Tyr Val Pro Xaa Ser Ser Tyr Leu
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 152

Lys Tyr Leu Pro Xaa Ser Asn Tyr Leu
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 153

Lys Tyr Asn Val Xaa Ser Asn Tyr Leu
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (5)..(5)
<223> OTHER INFORMATION: Dap
<220> FEATURE:
<221> NAME/KEY: MISC_FEATURE
<222> LOCATION: (5)..(9)
<223> OTHER INFORMATION: Cyclic

<400> SEQUENCE: 154

Lys Tyr Val Pro Xaa Ser Asn Tyr Leu
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (3)..(3)
<223> OTHER INFORMATION: Asn, Leu or Val
<220> FEATURE:
<221> NAME/KEY: MOD_RES
<222> LOCATION: (4)..(4)
<223> OTHER INFORMATION: Pro or Val
<220> FEATURE:
<221> NAME/KEY: MOD_RES
<222> LOCATION: (5)..(5)
<223> OTHER INFORMATION: Cys or Dab
<220> FEATURE:
<221> NAME/KEY: MISC_FEATURE
<222> LOCATION: (5)..(9)
<223> OTHER INFORMATION: Cyclic
<220> FEATURE:
<221> NAME/KEY: MOD_RES
<222> LOCATION: (6)..(6)
<223> OTHER INFORMATION: Ala or Ser
<220> FEATURE:
<221> NAME/KEY: MOD_RES
<222> LOCATION: (7)..(7)
<223> OTHER INFORMATION: Asn, Ala or Ser

<400> SEQUENCE: 155

Lys Tyr Xaa Xaa Xaa Xaa Xaa Tyr Leu
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 156

Asp Ala Val Cys Ala Ser Tyr Phe
1               5

<210> SEQ ID NO 157
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 157

Asp Ser Ala Cys Ala Ser Tyr Phe
1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 158

Asp Ser Val Cys Ala Ser Ala Phe
1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 159

Asp Ser Val Cys Ala Ser Tyr Ala
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MISC_FEATURE
<222> LOCATION: (4)..(8)
<223> OTHER INFORMATION: Cyclic

<400> SEQUENCE: 160

Asp Ser Val Cys Ala Ser Tyr Phe
1               5

<210> SEQ ID NO 161
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MISC_FEATURE
<222> LOCATION: (4)..(8)
<223> OTHER INFORMATION: Cyclic

<400> SEQUENCE: 161

Asp Ser Val Cys Ala Ser Tyr Phe
1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-amino acid
<220> FEATURE:
<221> NAME/KEY: MISC_FEATURE
<222> LOCATION: (4)..(8)
<223> OTHER INFORMATION: Cyclic

<400> SEQUENCE: 162

Asp Ser Val Cys Ala Ser Tyr Phe
1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic
<220> FEATURE:
<221> NAME/KEY: MOD_RES
<222> LOCATION: (5)..(5)
<223> OTHER INFORMATION: D-amino acid

<400> SEQUENCE: 163

Asp Ser Val Cys Ala Ser Tyr Phe
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic
<220> FEATURE:
<221> NAME/KEY: MOD_RES
<222> LOCATION: (6)..(6)
<223> OTHER INFORMATION: D-amino acid

<400> SEQUENCE: 164
```

```
Asp Ser Val Cys Ala Ser Tyr Phe
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic
<220> FEATURE:
<221> NAME/KEY: MOD_RES
<222> LOCATION: (7)..(7)
<223> OTHER INFORMATION: D-amino acid

<400> SEQUENCE: 165

Asp Ser Val Cys Ala Ser Tyr Phe
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic
<220> FEATURE:
<221> NAME/KEY: MOD_RES
<222> LOCATION: (8)..(8)
<223> OTHER INFORMATION: D-amino acid

<400> SEQUENCE: 166

Asp Ser Val Cys Ala Ser Tyr Phe
1               5

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (8)..(12)
<223> OTHER INFORMATION: Cyclic

<400> SEQUENCE: 167

Asn Ala Ser Lys Tyr Asn Pro Cys Ser Asn Tyr Leu
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (8)..(12)
<223> OTHER INFORMATION: Cyclic
```

<400> SEQUENCE: 168

Asn Ala Ala Lys Tyr Asn Pro Cys Ala Ser Tyr Leu
1               5                   10

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Acetylation
<220> FEATURE:
<221> NAME/KEY: MISC_FEATURE
<222> LOCATION: (1)..(5)
<223> OTHER INFORMATION: Cyclic

<400> SEQUENCE: 169

Cys Ala Ser Tyr Phe
1               5

<210> SEQ ID NO 170
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (7)..(11)
<223> OTHER INFORMATION: Cyclic

<400> SEQUENCE: 170

Ala Ser Lys Tyr Asn Pro Cys Ser Asn Tyr Leu
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (6)..(10)
<223> OTHER INFORMATION: Cyclic

<400> SEQUENCE: 171

Ser Lys Tyr Asn Pro Cys Ser Asn Tyr Leu
1               5                   10

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 172

Lys Tyr Asn Pro Cys Ser Asn Tyr Leu
1               5

```
<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 173

Tyr Asn Pro Cys Ser Asn Tyr Leu
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(7)
<223> OTHER INFORMATION: Cyclic

<400> SEQUENCE: 174

Asn Pro Cys Ser Asn Tyr Leu
1               5

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Acetylation
<220> FEATURE:
<221> NAME/KEY: MISC_FEATURE
<222> LOCATION: (1)..(5)
<223> OTHER INFORMATION: Cyclic

<400> SEQUENCE: 175

Cys Ser Asn Tyr Leu
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 176

Lys Tyr Leu Pro Cys Ser Asn Tyr Leu
1               5

<210> SEQ ID NO 177
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 177

Lys Tyr Val Pro Cys Ser Asn Tyr Leu
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 178

Lys Tyr Asn Val Cys Ser Asn Tyr Leu
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 179

Lys Tyr Asn Val Cys Ala Asn Tyr Leu
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic

<400> SEQUENCE: 180

Lys Tyr Asn Val Cys Ser Ala Tyr Leu
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(9)
<223> OTHER INFORMATION: Cyclic
```

<400> SEQUENCE: 181

Lys Tyr Asn Val Cys Ser Ser Tyr Leu
1               5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(8)
<223> OTHER INFORMATION: Cyclic

<400> SEQUENCE: 182

Tyr Asn Val Cys Ser Ala Tyr Leu
1               5

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MISC_FEATURE
<222> LOCATION: (4)..(8)
<223> OTHER INFORMATION: Cyclic

<400> SEQUENCE: 183

Asp Ser Val Cys Ala Ser Tyr Phe
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(7)
<223> OTHER INFORMATION: Cyclic

<400> SEQUENCE: 184

Ile Asn Cys Ala Phe Phe Leu
1               5

PEPTIDIC MODULATORS OF QUORUM SENSING IN *STAPHYLOCOCCUS EPIDERMIDIS*

CROSS-REFERENCE TO RELATED APPLICATION

This application is a U.S. National Stage Application under 35 U.S.C. § 371 of International Application No. PCT/US2017/030388, filed May 1, 2017, which claims the benefit of U.S. provisional application 62/330,211, filed May 1, 2016. Each of these applications is incorporated by reference herein in its entirety.

STATEMENT REGARDING FEDERALLY SPONSORED RESEARCH OR DEVELOPMENT

This invention was made with government support under N00014-14-1-0791 awarded by the NAVY/ONR. The government has certain rights in the invention.

SEQUENCE LISTING

The instant application contains a Sequence Listing which has been submitted electronically in ASCII format and is hereby incorporated by reference in its entirety. Said ASCII copy, originally created on Sep. 19, 2017, and amended Oct. 31, 2018, is named 336631_SL.txt and is 58 Kbytes in size.

BACKGROUND

*Staphylococcus epidermidis* is a ubiquitous commensal colonizer of human epithelia (1). Previously thought to be innocuous, *S. epidermidis* recently has been identified as an important nosocomial pathogen (2, 3). In particular, *S. epidermidis* is a leading causative agent in infections associated with indwelling medical devices, which is directly related to its ubiquity and propensity to form biofilms on abiotic surfaces (3-6). The barrier provided by this biofilm lifestyle, combined with growing resistance to antibiotics, make *S. epidermidis* infections especially recalcitrant to traditional antimicrobial treatments and, consequently, a serious problem to public health (2, 3, 6-8).

Playing an important role in the virulence of *S. epidermidis* is its quorum sensing (QS) system (9-13). QS is a cell-cell communication process that allows bacteria to sense population density and coordinate gene expression to control group behavior at high cell numbers (14, 15). The primary QS circuit in *S. epidermidis* is the accessory gene regulator (agr) system, which was first characterized and has been most studied to date in the related human pathogen *Staphylococcus aureus* (16-18). The agr system consists of four components (AgrA-D) that are encoded by the agr locus (FIG. 1) (16-19). AgrD is a propeptide containing the sequence of the mature autoinducing peptide (or AIP) signal, and it is processed and secreted by the integral membrane endopeptidase AgrB (20, 21). Once reaching a threshold extracellular concentration (produced by a "quorate" population of cells), the AIP is sensed by a two-component system comprised of AgrC and AgrA. Productive binding of the AIP to AgrC, a transmembrane receptor histidine kinase, triggers its subsequent dimerization and trans-autophosphorylation (22, 23); the activated AgrC then phosphorylates the response regulator AgrA. Phosphorylated AgrA next dimerizes, binds the P2 and P3 promoters, and upregulates the transcription of the agr locus and RNAIII, respectively. RNAIII serves as the main effector of the agr system, and thereby, many virulence phenotypes in *S. epidermidis* (24). Phosphorylated AgrA also directly activates the production of a group of small amphipathic peptides known as phenol-soluble modulins (PSMs), which are key virulence factors for both the biofilm life cycle and survival in infected hosts (11, 25).

The formation of a robust biofilm is the primary mechanism by which *S. epidermidis* causes infections on medical implants (3). A number of studies have identified the polysaccharide intercellular adhesin (PIA) as being a critical structural component of the biofilm (26). In *S. epidermidis* strains that produce PIA, the agr system is involved in many of the distinct stages of biofilm formation (10, 27, 28). Specifically, the agr system negatively regulates the expression of the surface-attached AtlE protein (29), an important adhesion factor in the attachment phase of biofilm growth, and positively regulates the production of PSMs and proteases that facilitate the detachment of bacteria from biofilm (11, 30, 31). Consequently, intentional activation of the agr system can provide an alternative approach of limiting *S. epidermidis* infection by reducing biofilm growth (32), especially considering that *S. epidermidis*, unlike *S. aureus*, does not possess a vast repertoire of damaging toxins under QS control (3, 18). Furthermore, this approach could be combined with administration of antibiotics to potentiate the effectiveness of such drugs (4, 32).

In contrast, other studies have proposed that inhibition, as opposed to activation, of the agr system can also attenuate virulence, despite the concern over the enhanced accumulation of biofilm observed in *S. epidermidis* agr mutants (28, 33, 34). For example, Otto and co-workers, using agr-null strains of *S. epidermidis*, have demonstrated that the presence of an active agr system offers the bacterium significantly more protection against antimicrobial peptides and oxidative stress, both of which are defense mechanisms against infections employed by the innate immune system (10, 13). The agr system has also been shown to promote bacteria dissemination and tissue infiltration during device-related infections (13, 30, 31, 35). Further, a recent report by Olson et al. revealed the agr system to be necessary for optimal skin colonization (36). Lastly, there is growing appreciation that many *S. epidermidis* clinical isolates from implant infections do not have the genes to make PIA (37-39), but these strains still build a biofilm (40). The role the agr system plays in biofilm development in these PIA-negative strains is unclear. Combined, these studies and others highlight the complex roles played by the agr system in the lifestyle of *S. epidermidis*. Therefore, while the agr system is an attractive target for controlling the virulence of *S. epidermidis*, further fundamental studies are required to assess when and how the agr system should be modulated (either via activation or inhibition) to attenuate infection.

Similar to *S. aureus*, the agr system is not identical within the *S. epidermidis* species. Based upon the primary structures of the three reported AIP signals (I-III) (FIG. 1B), *S. epidermidis* can be classified into three agr specificity groups referred to as Groups-I-III (36, 41). Interestingly, the agr systems of these groups are known to interact with each other, a phenomenon called agr interference that was first described in *S. aureus* (18, 42-44). In *S. epidermidis*, the agr system of Group-I is significantly inhibited by the AIP-II and -III signals, whereas Groups-II and -III are inhibited by AIP-I (36). In addition, agr interference has also been identified between *S. epidermidis* Group-I and *S. aureus* Groups-I-IV, two species that colonize similar environmental niches on the human body (45-47). These cross-inhibitory activities of the agr systems between different specificity groups and species have been hypothesized to play a role in competition for colonization and establishing infections (18, 46, 48). However, in vivo studies have not provided conclusive support for such hypothesis (48, 49). Additional studies are therefore necessary to elucidate the biological significance of agr interference, if any.

Chemical methods to modulate QS in bacteria have attracted considerable interest over the past decade, due in part to the temporal and spatial control they can provide and their often ready applicability to biologically relevant environments (50-52). The development of chemical probes capable of modulating the *S. epidermidis* agr system can provide valuable tools for better understanding the role of the agr system in colonization and infection by this common bacterium. Both agr agonists and antagonists are of interest, given the dynamic and complex role played by QS during *S. epidermidis* infection. Moreover, identification of modulators that can selectively target a specific agr group or Staphylococcal species in a mixed bacteria population would provide promising tools to investigate the role of QS in the interplay between different agr groups or species. Prior studies by our lab and others have focused on the structure-activity relationships (SARs) for AIP:AgrC interactions in *S. aureus*, and have uncovered a number of potent, non-native *S. aureus* AgrC inhibitors in the process (43, 53-61). Little is known, however, about the SARs of AIP:AgrC interactions in *S. epidermidis*. Earlier work by Otto and co-workers has shown that the thioester linkage and the three-amino acid exocyclic tail of AIP-I (FIG. 1B) are required for AgrC-I activation, as they found the hydrolyzed acyclic AIP-I, AIP-I analogs with exocyclic tails either one amino acid shorter or longer, and AIP-I analogs with a lactam or a lactone in place of the thioester were all inactive in cell-based AgrC-I activation assays (47, 62). However, to our knowledge, no non-native AgrC agonists and antagonists have been reported for *S. epidermidis* to date.

SUMMARY

This disclosure provides modulators of the AgrC quorum sensing system of *S. epidermidis* of AgrC. Synthetic agonists and antagonist are identified. The compounds herein are identified by a systematic analysis of the *S. epidermidis* AIP-I structure and key SARs for AgrC-I activation are identified. AIP-I analogs that antagonize or agonize the AgrC-I receptor are provided. Certain synthetic analogs very strongly antagonize or agonize the AgrC-I. Several of the compounds identified are capable of either pan-group or group-selective AgrC receptor inhibition in *S. epidermidis*. Other compounds were found to be species selective, and can be applied to selectively modulate either *S. epidermidis* or *S. aureus* AgrC receptors. Notably, certain non-native AgrC-I agonists strongly inhibit *S. epidermidis* biofilm growth, with a higher potency and efficacy than that of native AIP-I. These new compounds represent the first synthetic modulators of AgrC in *S. epidermidis* and constitute powerful tools for modulation of virulence in *S. epidermidis* and related *Staphylococcus* (e.g., *S. aureus*) and as research tools to elucidate the complex roles of the agr QS system in this emerging pathogen.

The disclosure provides methods of modulating virulence in *S. epidermidis* and related *Staphylococcus* which are of particular use with *S. epidermidis* and other *Staphylococcus* that form biofilms by contacting a bacterium or a bacterial environment (e.g., a biofilm) with a modulator of the disclosure.

The disclosure provides methods of treating infections of *S. epidermidis* and related *Staphylococcus* by administering a therapeutically effective amount of one or more compounds of the disclosure to an individual in need thereof.

Other aspects of the invention will be apparent to one of ordinary skill in the art on review of the description and drawings herein.

BRIEF DESCRIPTION OF THE DRAWINGS

FIG. 1A is a simplified schematic of the agr system. Propeptide AgrD is processed and secreted by the integral membrane endopeptidase AgrB to generate the mature autoinducing peptide (AIP) signal. Once a threshold extracellular concentration of AIP is reached, the AgrC receptor binds to its cognate AIP and homodimerizes. Activation of AgrC, a transmembrane histidine kinase, by AIP leads to AgrC trans-autophosphorylation, which then phosphorylates the response regulator AgrA. The phosphorylated AgrA subsequently activates transcription from the P2, P3, and PSM promoters. P2 encodes the four components of the agr system, whereas P3 drives the expression of RNAIII, the main effector molecule of the agr system. FIG. 1B shows the primary structures of the three AIP signals (I-III) (SEQ ID NOS 68, 167, and 168, respectively) corresponding to the three *S. epidermidis* agr Groups (I-III).

FIG. 2A is a graph illustrating the effects of AIP-I analogs on AgrC-I-III as determined by fluorescence reporter strains (see Methods for details of strains and assay procedures). Compounds were tested at either 10 µM (indicated with *) or 100 nM. Effects for Groups are shown in the order: Black: Group-I; Gray: Group-II; White: Group-III. FIG. 2B is a Venn diagram summarizing agr group selectivity profiles for AgrC inhibition by AIP analogs in *S. epidermidis*. AIP-II 8aa shows differential selectivity at *10 µM and at 100 nM. *Compound is an agonist of AgrC-II. FIG. 2B discloses SEQ ID NOS 172, 175, 173, 184, 173, 94, 95, and 161, respectively, in order of appearance.

FIG. 7A shows the effects of alanine and D-amino acid analogs of S. epidermidis AIP-I on S. epidermidis AgrCs I-III, bars 1-3, respectively shown sequentially along x-axis in graph. FIG. 7B shows the effects of the second-generation S. epidermidis AIP analogs and S. aureus AIP-III D4A on S. epidermidis AgrCs I-III, bars 1-3, respectively shown sequentially along x-axis in graph. FIG. 7C shows the effects of selected S. epidermidis AIP analogs and S. aureus AIP-III D4A on S. epidermidis AgrCs I-III, bars 1-3, respectively shown sequentially along x-axis in graph. Compounds were tested at 100 nM unless otherwise noted. * Compound tested at 1 μM. FIG. 7D shows the effects of selected S. epidermidis AIP analogs and S. aureus AIP-III D4A on S. aureus AgrCs I-IV, bars 1-4, respectively shown sequentially along x-axis in graph. Compounds were tested at 100 nM unless otherwise noted. * Compound was tested at 1 μM.

FIG. 10A indicates that S. epidermidis AIP-II 9aa N3L (K-Y-L-P-C-S-N-Y-L) (SEQ ID NO: 1) is an antagonist of S. epidermidis Group I (filled circles) and Group II (filled squares), but more active in Group I. FIG. 10B indicates that S. epidermidis AIP-II 9aa N3V (K-Y-V-P-C-S-N-Y-L) (SEQ ID NO: 2) is an antagonist of both S. epidermidis Group I (filled circles) and Group II (filled squares), but more active in Group I. FIG. 10C indicates that S. epidermidis AIP-II 9aa P4V (K-Y-N-V-C-S-N-Y-L) (SEQ ID NO: 3) is an antagonist of S. epidermidis Group I (filled circles), yet a potent agonist of S. epidermidis Group II (filled squares).

FIG. 11A indicates that S. epidermidis AIP-II 9aa P4VS6A (K-Y-N-V-C-A-N-Y-L) (SEQ ID NO: 4) is inactive towards S. epidermidis Group I (filled circles) but antagonistic toward S. epidermidis Group II (filled squares). FIG. 11B indicates that S. epidermidis AIP-II 9aa P4VN7A (K-Y-N-V-C-S-A-Y-L) (SEQ ID NO: 5) is an agonist of both S. epidermidis Group I (filled circles) and Group II (filled squares). FIG. 11C indicates that S. epidermidis AIP-II 9aa P4VN7S (K-Y-N-V-C-S-S-Y-L) (SEQ ID NO: 6) is an agonist for S. epidermidis Group II (filled squares), and an antagonist for S. epidermidis Group I (filled circles).

DETAILED DESCRIPTION OF THE INVENTION

Figure 1A:
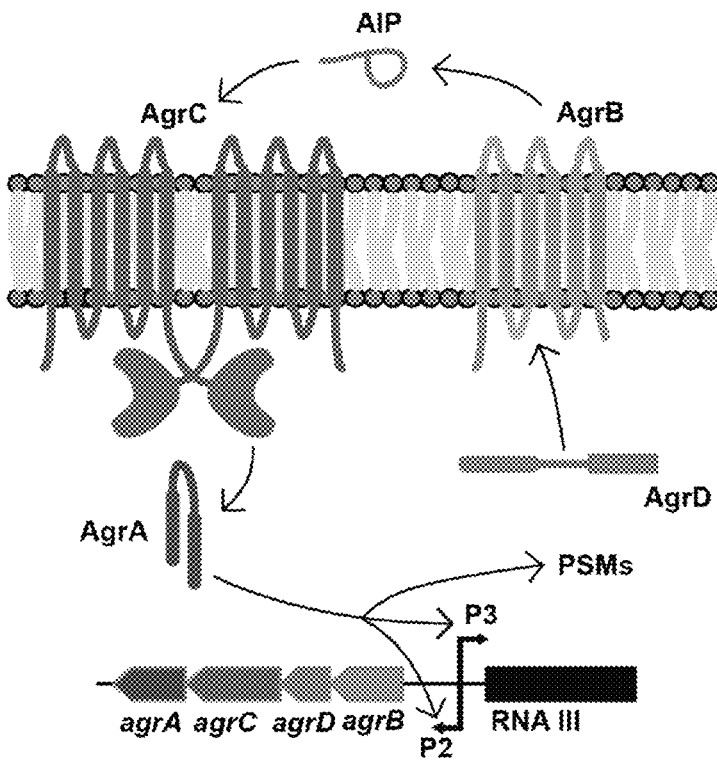
FIGS. 1A and 1B illustrate the agr QS system in *S. epidermidis* and associated AIP signals.
Figure 1B:
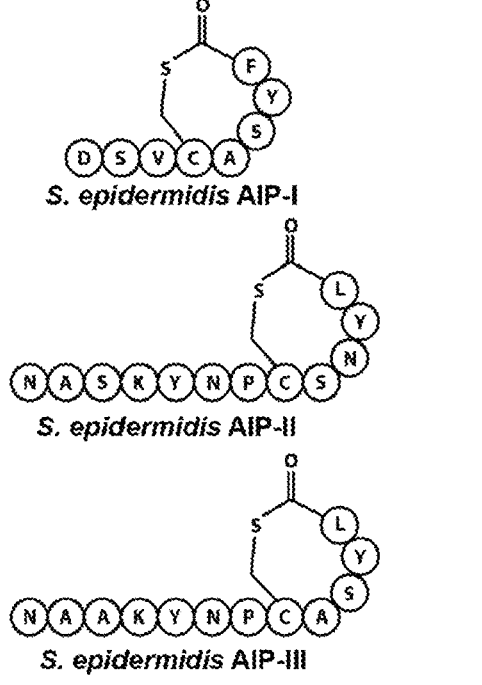

The disclosure provides quorum sensing modulators of certain Staphylococcus, particularly of the AgrC-I receptor of S. epidermidis and AgrC of related Staphylococcus (e.g., S. aureus). The modulators herein are of formula I:

or salts thereof,
where:

X is S, NH, or N(CH$_3$); each R$_{N1}$-R$_{N5}$ is independently H or CH$_3$;

R$_1$ is an alkyl group having 1-6 carbon atoms, or a phenyl or a benzyl group which is optionally substituted;

R$_2$ is an alkyl having 1-6 carbon atoms, or a phenyl or a benzyl group which is optionally substituted;

R$_3$ is an alkyl group having 1-6 carbon atoms, a γ-hydroxyalkyl group having 1-6 carbon atoms, or a γ-CONH$_2$-substituted alkyl group having 1-6 carbon atoms;

R$_4$ is an alkyl group having 1-6 carbon atoms, a phenyl or a benzyl group which is optionally substituted or a γ-hydroxyalkyl group having 1-6 carbon atoms;

R$_T$ is an alkyl group having 1-6 carbon atoms, hydrogen, a hydroxyl, or —OR, where R is hydrogen or an alkyl having 1-6 carbon atoms, or R$_T$—CO is an optionally N-methylated peptide ranging in length from 1 to 7 amino acids; and where substitution of phenyl or benzyl groups, when present, includes substitution with one or more non-hydrogen groups selected from halogen, hydroxyl, alkyl having 1-3 carbon atoms, amino-substituted alkyl having 1-4 carbon atoms, alkoxy having 1-3 carbon atoms, amino, alkylamino having 1-3 carbon atoms, dialkyl amino where the alkyl group has 1-3 carbon atoms, haloalkyl having 1-3 carbon atoms, haloalkoxyl having 1-3 carbon atoms, sulfhydryl, alkylthio having 1-3 carbon atoms, —CO$_2$R where R is hydrogen or an alkyl having 1-3 carbon atoms, —COR, where R is H or an alkyl having 1-3 carbon atoms, —CO—NR$_2$, where each R is independently hydrogen or alkyl having 1-3 carbon atoms, azido (—N$_3$), nitro, cyano, isocyano, thiocyano, isothiocyano, cyanate, isocyanate, thiocyanate, isothiocyanate. Preferred substitution is substitution with one or more halogen, hydroxyl or methyl. Substitution includes substitution with 1-3 substituents. Substitution includes substitution with one substituent.

In an embodiment, the disclosure is directed to one or more compounds of formula I with the exception that the compound is not AIP-I, AIP-II, AIP-III, I-N-(C-A-F-L-L) (SEQ ID NO: 7), Y-S-T-(C-D-F-I-M) (SEQ ID NO: 8), G-V-N-A-(C-S-S-L-F) (SEQ ID NO: 9), I-N-(C-D-F-L-L) (SEQ ID NO: 10) or Y-S-T—(C-Y-F-I-M) (SEQ ID NO: 11).

In specific embodiments, $R_1$ is a branched alkyl having 3-5 carbon atoms. In specific embodiments, $R_1$ is an optionally substituted phenyl or benzyl group. In specific embodiments, $R_1$ is an optionally substituted benzyl group. In specific embodiments, $R_1$ is a para-substituted phenyl or benzyl. In specific embodiments, $R_1$ is a phenyl or benzyl ring substituted with a halogen, OH, methyl or methoxy group. In specific embodiments, $R_1$ is a benzyl substituted in the para ring position with a halogen, OH, methyl or methoxy group. In specific embodiments, $R_1$ is an unsubstituted benzyl.

In specific embodiments, $R_2$ is a branched alkyl having 3-5 carbon atoms. In specific embodiments, $R_2$ is an optionally substituted phenyl or benzyl group. In specific embodiments, $R_2$ is an optionally substituted benzyl group. In specific embodiments, $R_2$ is a para-substituted phenyl or benzyl. In specific embodiments, $R_2$ is a phenyl or benzyl ring substituted with a halogen, OH, methyl or methoxy group. In specific embodiments, $R_2$ is a benzyl substituted in the para ring position with a halogen, OH, methyl or methoxy group. In specific embodiments, $R_2$ is an unsubstituted benzyl.

In specific embodiments, both of $R_1$ and $R_2$ are optionally substituted phenyl or benzyl groups. In specific embodiments, both of $R_1$ and $R_2$ are optionally substituted benzyl groups. In specific embodiments, both of $R_1$ and $R_2$ are unsubstituted benzyl groups. In specific embodiments, one or $R_1$ and $R_2$ is an optionally substituted benzyl group and the other of $R_1$ and $R_2$ is an unsubstituted benzyl group. In specific embodiments, one of $R_1$ and $R_2$ is a branched alkyl group having 3-5 carbon atoms and the other of $R_1$ and $R_2$ is an optionally substituted phenyl or benzyl group. In specific embodiments, one of $R_1$ and $R_2$ is a branched alkyl group having 3-5 carbon atoms and the other of $R_1$ and $R_2$ is an unsubstituted benzyl group or a para-substituted benzyl group. In specific embodiments, one of $R_1$ and $R_2$ is a branched alkyl group having 3-5 carbon atoms and the other of $R_1$ and $R_2$ is an unsubstituted benzyl group or a para-substituted benzyl group where the para-substituent is OH, halogen, methyl or methoxy.

In specific embodiments, $R_3$ is an alky group having 1-3 carbon atoms. In specific embodiments, $R_3$ is —$(CH_2)_{1-3}$—OH. In specific embodiments, $R_3$ is —$(CH_2)_{1-3}$—$CONH_2$. In specific embodiments, $R_3$ is a $CH_3$ group. In specific embodiments, $R_3$ is —$CH_2$—OH. In specific embodiments, $R_3$ is —$CH_2CONH_2$.

In specific embodiments, $R_4$ is an alky group having 1-3 carbon atoms. In specific embodiments, $R_4$ is —$(CH_2)_{1-3}$—OH. In specific embodiments, $R_4$ is a $CH_3$ group. In specific embodiments, $R_4$ is —$CH_2$—OH.

In specific embodiments of formulas herein, phenyl and benzyl groups are optionally substituted with one or more halogen, OH, $CH_3$, $OCH_3$, —$NH_2$, $CF_3$, SH, $SCH_3$, COH, $COCH_3$, $N_3$, $NO_2$, or CN. In more specific embodiments, phenyl and benzyl groups are optionally substituted with one or more halogen, OH, $CH_3$, $OCH_3$, $CF_3$, $N_3$, $NO_2$, or CN. In more specific embodiments, phenyl and benzyl groups are optionally substituted with one or more halogen, OH, $CH_3$, $OCH_3$, $CF_3$, or $NO_2$. In more specific embodiments, phenyl and benzyl groups are optionally substituted with one or more Cl, F, Br, I, OH, $CH_3$, $OCH_3$, $CF_3$, $N_3$, $NO_2$, or CN. In more specific embodiments, phenyl and benzyl groups are optionally substituted with one or more F, OH, $CH_3$, $OCH_3$, $CF_3$, or $NO_2$. In more specific embodiments, phenyl and benzyl groups are substituted with one substituent at the para-ring position (with respect to the groups' bond to the compound). In more specific embodiments, phenyl and benzyl groups are substituted at the para-ring position with F, OH or $CH_3$.

In specific embodiments, X is NH or $N(CH_3)$. In specific embodiments, X is NH. In specific embodiments, X is $N(CH_3)$.

In specific embodiments, $R_{N5}$ is $CH_3$. In specific embodiments, $R_{N4}$ is $CH_3$. In specific embodiments, $R_{N3}$ is $CH_3$. In specific embodiments, $R_{N2}$ is $CH_3$. In specific embodiments, $R_{N1}$ is $CH_3$. In specific embodiments, each of $R_{N1}$-$R_{N4}$ is $CH_3$. In specific embodiments, each of $R_{N1}$-$R_{N5}$ is $CH_3$. In specific embodiments, each of $R_{N1}$ and $R_{N4}$ is $CH_3$. In specific embodiments, each of $R_{N2}$ and -$R_{N3}$ is $CH_3$.

In specific embodiments, $RN_1$-$R_{N5}$ are hydrogen.

In specific embodiments, X is S.

In specific embodiments, $R_7CO$ is

P7

P6

P5

-continued

P4                                                                                 P3

P2                                                                                 P1 or salts thereof,
where:
each $R_{N6}$-$R_{N12}$ is independently hydrogen or $CH_3$;

$R_6$ is an alkyl group having 1-6 carbon atoms, or $R_6$ and $R_{N6}$ together with the nitrogen to which $R_{N6}$ is bonded form a 5 or 6 member ring;

$R_7$ is an alkyl group having 1-6 carbon atoms, a γ-substituted hydroxyalkyl group having 1-6 carbon atoms; or a γ-CO—$NH_2$-substituted alkyl group having 1-6 carbon atoms;

$R_8$ is an alkyl group having 1-6 carbon atoms, a γ-substituted hydroxyalkyl group having 1-6 carbon atoms, a phenyl group or a benzyl group where the phenyl or benzyl group is optionally substituted (as described above);

$R_9$ is an alkyl having 1-3 carbon atoms, hydrogen or a γ-aminoalkyl group having 1-6 carbon atoms;

$R_{10}$ is an alkyl group having 1-3 carbon atoms, or a γ-hydroxyalkyl group having 1-3 carbon atoms;

$R_{11}$ is an alkyl group having 1-3 carbon atoms; and $R_{12}$ is an alkyl group having 1-6 carbon atoms, or a γ-CO—$NH_2$-substituted alkyl group having 1-6 carbon atoms.

In specific embodiments, $R_7CO$ is P3 or P4. In specific embodiments, the alkyl groups or substituted alkyl groups of $R_8$, $R_9R_{10}$, $R_{11}$ or $R_{12}$ are straight-chain alkyl groups. In specific embodiments, at least one of the alkyl groups of $R_6$ or $R_7$ is a branched alkyl group. In specific embodiments, $R_{10}$ is an alkyl group. In specific embodiments, two of $R_6$-$R_8$ are alkyl groups. In specific embodiments, $R_6$ is a branched alkyl group. In specific embodiments, $R_7$ is a branched alkyl group. In specific embodiments, $R_6$ and $R_{N6}$ together with the nitrogen to which $R_{N6}$ is bonded form a 5 member ring (forming Pro). In specific embodiments, $R_6$ and $R_{N6}$ together with the nitrogen to which $R_{N6}$ is bonded form a 5 member ring (forming Pro) and R7 is a branched alkyl group having 3-6 carbon atoms.

In specific embodiments, $R_{12}$ is —$(OH_2)_{1-3}$—$NH_2$. In specific embodiments, $R_{12}$ is —$CH_2$—$NH_2$. In specific embodiments, $R_{11}$ is methyl. In specific embodiments, $R_{10}$ is an alkyl having 1-3 carbon atoms. In specific embodiments, $R_{10}$ is methyl. In specific embodiments, $R_{10}$ is —$(CH_2)_{1-3}OH$. In specific embodiments, $R_{10}$ is —$CH_2$—OH. In specific embodiments, $R_9$ is —$(CH_2)_{3-5}$—$NH_2$. In specific embodiments, $R_9$ is —$(CH_2)_4$—$NH_2$. In specific embodiments, $R_8$ is an optionally substituted phenyl or benzyl group. In specific embodiments, $R_8$ is an optionally substituted benzyl group. In specific embodiments, $R_8$ is a phenyl or benzyl group substituted at the para ring position with F, OH, $CH_3$ or $CF_3$. In specific embodiments, $R_8$ is a benzyl group substituted at the para ring position with F, OH, $CH_3$ or $CF_3$. In specific embodiments, $R_8$ is a benzyl group substituted in the para position with F or OH. In specific embodiments, $R_8$ is a para-OH benzyl group. In specific embodiments, $R_8$ is an unsubstituted benzyl group. In specific embodiments, $R_7$ is iso-propyl, iso-butyl or sec-butyl. In specific embodiments, $R_7$ is iso-propyl. In specific embodiments, $R_7$ is —$(OH_2)_{1-3}$—$CONH_2$ or —$(CH_2)_{1-3}$—OH. In specific embodiments, $R_7$ is —$CH_2$—OH. In specific embodiments, $R_7$ is —$CH_2$—$CONH_2$.

In specific embodiments of P3 and P4, $R_8$ is an alkyl having 1-3 carbon atoms, $R_7$ is a γ-hydroxyalkyl having 1-3 carbons atoms and $R_6$ is a straight-chain alkyl having 1-3 carbon atoms. In specific embodiments of P3 and P4, $R_8$ is an alkyl having 1-3 carbon atoms, $R_7$ is a γ-hydroxyalkyl having 1-3 carbons atoms and $R_6$ is a branched alkyl having 3-5 carbon atoms. In specific embodiments of P3 and P4, $R_8$ is an alkyl having 1-3 carbon atoms, $R_7$ is a γ-hydroxyalkyl having 1-3 carbons atoms and $R_6$ is a straight chain alkyl having 1-3 carbon atoms.

In specific embodiments of P4, $R_9$ is hydrogen, $R_8$ is an alkyl group having 1-6 carbon atoms, $R_7$ is a —$(CH_2)_{1-3}$—$CONH_2$ group, and $R_6$ is an alkyl group having 1-3 carbon atoms. In specific embodiments of P4, $R_9$ is hydrogen, $R_8$ is a branched alkyl group having 3-5 carbon atoms, $R_7$ is a —$(CH_2)$—$CONH_2$ group, and $R_6$ is an alkyl group having 1-3 carbon atoms. In specific embodiments of P4, $R_9$ is hydrogen, $R_8$ is a branched alkyl group having 3-5 carbon atoms, $R_7$ is a —$(CH_2)$—$CONH_2$ group, and $R_6$ is a methyl group.

In specific embodiments, each of $R_{N12}$-$R_{N6}$ is $CH_3$, except when $R_6$ together with $R_{6N}$ forms a ring. In specific embodiments, each of $R_{N12}$-$R_{N6}$ is hydrogen, except when $R_6$ and $R_{6N}$ together form a ring. In a specific embodiment of P7, each of $R_{N12}$ is a $CH_3$. In a specific embodiment of P6, each of $R_{N11}$ is a $CH_3$. In a specific embodiment of P5, each of $R_{N10}$ is a $CH_3$. In a specific embodiment of P4, each of $R_{N9}$ is a $CH_3$. In a specific embodiment of P3, each of $R_{N8}$ is a $CH_3$. In a specific embodiment of P2, each of $R_{N7}$ is a $CH_3$. In a specific embodiment of P1, each of $R_{N6}$ is a $CH_3$, except when $R_6$ and $R_{6N}$ together form a ring. In a specific embodiment of P7, each of $R_{N12}$ is H. In a specific embodiment of P6, each of $R_{N11}$ is a H. In a specific embodiment of P5, each of $R_{N10}$ is H. In a specific embodiment of P4, each of $R_{N9}$ is H. In a specific embodiment of P3, each of $R_{N8}$ is H. In a specific embodiment of P2, each of $R_{N7}$ is H. In a specific embodiment of P1, each of $R_{N6}$ is H, except when $R_6$ and $R_{6N}$ together form a ring. In specific embodiments, each of $RN_{12}$-$R_{N6}$, which is not at the N-terminus of the peptide is $CH_3$.

The disclosure is also directed to a method of modulating quorum sensing in a *Staphylococcus* strain. In specific embodiments, the *Staphylococcus* is *S. epidermidis* or *S.*

*aureus.* In specific embodiments, modulation of quorum sensing is modulation of virulence. In specific embodiments, modulation of virulence is inhibition of virulence. In specific embodiments, modulation of virulence is inhibition of bio-film formation or disruption of already-formed biofilms.

In specific embodiments, all amino acids of the compound of formula I are L-amino acids. In a specific embodiment, the amino acid with side chain $R_7$ can be an L-or a D-amino acid and all other amino acids are L-amino acids. In specific embodiments, all amino acids of the macrocycle are L-amino acids. In specific embodiments, all amino acids of the macrocycle are L-amino acids and any serine or alanine in the exocyclic tail of the compound is a D-amino acid.

In specific embodiments, $R_7CO$ is a peptide of formula A1-A7 or salts or methylated derivatives thereof:

| | |
|---|---|
| N-A-X10-K-X8-X7-X6- | A7 |
| A-X10-K-X8-X7-X6- | A6 |
| X10-K-X8-X7-X6- | A5 |
| K-X8-X7-X6- | A4 |
| X8-X7-X6- | A3 |
| X7-X6- | A2 |
| X6- | A1 | where:
  X10 is Ala or Ser;
  X8 is Ala, Asp or Try;
  X7 is Asn, Ile, Leu, Ser, or Val;
  X6 is Ala, Ile, Leu, Pro or Val, and
  when X6 is .Ile, Leu or Val, X7 can also be D-Asn or D-Ser, where methylated derivatives have at least one NH group of the peptide which is methylated.

In specific embodiments, $R_7CO$ is a peptide of formula A8 or salts or methylated derivatives thereof:

| | |
|---|---|
| G-X8-Asn-Ala- | A8 | where:
  X8 is Ile, Leu, or Val.

In specific embodiments of formula I, where the exocyclic tail of the compound is A8, the macrocycle of the peptide is: (C-S-N-Y-L) (SEQ ID NO: 12), (Dab-S-N-Y-L) (SEQ ID NO: 13), (C-A-A-Y-F) (SEQ ID NO: 14), (Dab-A-A-Y-F) (SEQ ID NO: 15), (C-S-A-Y-F) (SEQ ID NO: 16) or (Dab-S-A-Y-F) (SEQ ID NO: 17) or methylated derivatives thereof.

Conventional one (X) and three letter (XXX) abbreviations for L-amino acids are employed. D-amino acids if present are represented by $_DX$ or by D-XXX. In specific embodiments of A2-A7, one of X6 or X7 is Ile, Leu or Val. In specific embodiments X6 is Ala or Pro. In specific embodiments, A2 is Asn-Pro. In specific embodiments, A3 is Asp-Ser-X6, where X6 is Ile, Leu or Val. In specific embodiments A3 is Asp-Ser-Ala. In specific embodiments, A3 is Ala-Ser-X6, where X6 is Ile, Leu or Val. IN specific embodiments, A3 is Ala-Ser-Ala. In specific embodiments of A3-A7, X8-X7-X6 is Try, Asn, Pro.

In specific embodiments, the macrocycle of the compound of formula I is

| | |
|---|---|
| | (SEQ ID NO: 18) |
| (C-A-N-Y-L), | |
| | (SEQ ID NO: 19) |
| (C-A-N-Y-F), | |

-continued

| | |
|---|---|
| | (SEQ ID NO: 20) |
| (C-A-N-L-F), | |
| | (SEQ ID NO: 21) |
| (C-A-N-F-L), | |
| | (SEQ ID NO: 22) |
| (C-S-S-Y-L), | |
| | (SEQ ID NO: 23) |
| (C-S-S-Y-F), | |
| | (SEQ ID NO: 24) |
| (C-S-S-L-F), | |
| | (SEQ ID NO: 25) |
| (C-S-S-F-L), | |
| | (SEQ ID NO: 26) |
| (C-A-S-Y-L), | |
| | (SEQ ID NO: 27) |
| (C-A-S-Y-F), | |
| | (SEQ ID NO: 28) |
| (C-A-S-L-F), | |
| | (SEQ ID NO: 29) |
| (C-A-S-F-L), | |
| | (SEQ ID NO: 30) |
| (C-S-A-Y-L), | |
| | (SEQ ID NO: 16) |
| (C-S-A-Y-F), | |
| | (SEQ ID NO: 31) |
| (C-S-A-L-F), | |
| | (SEQ ID NO: 32) |
| (C-S-A-F-L), | |
| | (SEQ ID NO: 33) |
| (C-A-A-Y-L), | |
| | (SEQ ID NO: 14) |
| (C-A-A-Y-F), | |
| | (SEQ ID NO: 34) |
| (C-A-A-L-F), | |
| | (SEQ ID NO: 35) |
| (C-A-A-F-L), | |
| | (SEQ ID NO: 36) |
| (C-Y-S-Y-L), | |
| | (SEQ ID NO: 37) |
| (C-Y-S-Y-F), | |
| | (SEQ ID NO: 38) |
| (C-Y-S-L-F), | |
| | (SEQ ID NO: 39) |
| (C-Y-S-F-L), | |
| | (SEQ ID NO: 12) |
| (C-S-N-Y-L), | |
| | (SEQ ID NO: 40) |
| (C-S-N-Y-F), | |
| | (SEQ ID NO: 41) |
| (C-S-N-L-F), | |
| | (SEQ ID NO: 42) |
| (C-S-N-F-L), | |
| | (SEQ ID NO: 43) |
| (Dab-A-N-Y-L), | |

-continued (SEQ ID NO: 44)
(Dab-A-N-Y-F), (SEQ ID NO: 45)
(Dab-A-N-L-F), (SEQ ID NO: 46)
(Dab-A-N-F-L), (SEQ ID NO: 47)
(Dab-S-S-Y-L), (SEQ ID NO: 48)
(Dab-S-S-Y-F), (SEQ ID NO: 49)
(Dab-S-S-L-F), (SEQ ID NO: 50)
(Dab-S-S-F-L), (SEQ ID NO: 51)
(Dab-A-S-Y-L), (SEQ ID NO: 52)
(Dab-A-S-Y-F), (SEQ ID NO: 53)
(Dab-A-S-L-F), (SEQ ID NO: 54)
(Dab-A-S-F-L), (SEQ ID NO: 55)
(Dab-S-A-Y-L), (SEQ ID NO: 17)
(Dab-S-A-Y-F), (SEQ ID NO: 56)
(Dab-S-A-L-F), (SEQ ID NO: 57)
(Dab-S-A-F-L), (SEQ ID NO: 58)
(Dab-A-A-Y-L), (SEQ ID NO: 15)
(Dab-A-A-Y-F), (SEQ ID NO: 59)
(Dab-A-A-L-F), (SEQ ID NO: 60)
(Dab-A-A-F-L), (SEQ ID NO: 61)
(Dab-Y-S-Y-L), (SEQ ID NO: 62)
(Dab-Y-S-Y-F), (SEQ ID NO: 63)
(Dab-Y-S-L-F), (SEQ ID NO: 64)
(Dab-Y-S-F-L), (SEQ ID NO: 13)
(Dab-S-N-Y-L), (SEQ ID NO: 65)
(Dab-S-N-Y-F), (SEQ ID NO: 66)
(Dab-S-N-L-F), (SEQ ID NO: 67)
(Dab-S-N-F-L), or methylated derivatives thereof having at least one NH group methylated or salts thereof.

Modulators of the disclosure include methylated analogs of the compounds of formula I having 1-12 methylated NH groups dependent upon the length of the peptide.

The disclosure provides agonist compounds of formula II:

or salts thereof,
where:

X is S, NH, or $N(CH_3)$;

each $R_{N1}$-$R_{N5}$ is independently H or $CH_3$;

$R_1$ is a branched alkyl group having 3-6 carbon atoms, a phenyl group, or a benzyl group which is optionally substituted at the para-ring position;

$R_2$ is a branched alkyl group having 3-6 carbon atoms, a phenyl group, or a benzyl group which is optionally substituted at the para-ring position;

$R_3$ is an alkyl group having 1-3 carbon atoms or a $\gamma$-hydroxyalkyl group having 1-3 carbon atoms;

$R_4$ is an alkyl group having 1-3 carbon atoms;

$R_T$—CO is an optionally N-methylated peptide of three amino acids:

P3 where each $R_{N6}$-$R_{N8}$ are independently hydrogen or methyl;

$R_6$ is a branched alkyl group having 3-6 carbon atoms;

$R_7$ is an alkyl having 1-3 carbon atoms or a $\gamma$-hydroxyalkyl having 1-3 carbon atoms; and $R_8$ is an alkyl having 1-3 carbon atoms or —$(CH_2)_{1-3}$—COOH, with the exception that the compound is not D-S-V-(C-A-S-Y-F) (SEQ ID NO: 68).

In specific embodiments of formula II X is S. In specific embodiments of formula II X is NH or $N(CH_3)$.

In an embodiment, all amino acids of formula II are L-amino acids with the exception that the amino acid with side chain $R_7$ is an L- or a D-amino acid. In a specific embodiment, the compounds of formula II include those of optionally methylated cyclic peptide of formula B1:

X8-X7-X6-(X5-X4-X3-X2-X1)

where:

X8 is Ala, or Asp;

X7 is Ser or D-Ser;

X6 is Ile, Leu or Val;

X5 is Cys or Dab (Diaminopropionic acid);

X4 is Ala;

X3 is Ala or Serl ;

X2 is Ile, Leu, Val, Phe or Tyr; and

X1 is Ile, Leu, Val, Phe or Tyr, where one or more of the —NH groups of the peptide is optionally methylated and specifically the —NH— group of Dab in the macrocycle is optionally methylated.

In a specific embodiment, one or more of the NH groups of B1 are methylated. In a specific embodiment, all of the NH groups of the exocyclic-tail of B1 are methylated. In a specific embodiment, all NH groups of the B1 peptide are methylated. In a specific embodiment, none of the NH groups of the B1 macrocycle are methylated.

In specific embodiments, compounds of formula II include:

A-S-V-(C-A-A-Y-F) (SEQ ID NO: 69), A-S-I-(C-A-A-Y-F) (SEQ ID NO: 70), A-S-L-(C-A-A-Y-F) (SEQ ID NO: 71),

A-S-V-(C-A-S-Y-F) (SEQ ID NO: 72),

A-S-V-(Dab-A-A-Y-F) (SEQ ID NO: 73), A-S-I-(Dab-A-A-Y-F) (SEQ ID NO: 74), A-S-L-(Dab-A-A-Y-F) (SEQ ID NO: 75),

A-S-V-(Dab-A-S-Y-F) (SEQ ID NO: 76),

D-S-V-(C-A-A-Y-F) (SEQ ID NO: 77),

D-S-V-(Dab-A-A-Y-F) (SEQ ID NO: 78),

D-S-V-(Dab-A-S-Y-F) (SEQ ID NO: 79) or methylated derivatives thereof or

D-S-V-(C-A-S-Y-F) (SEQ ID NO: 68), wherein at least one NH group is methylated, particularly wherein at least one NH of the exocyclic tail is methylated, or salts thereof.

The disclosure provides antagonist compounds of formula III:

or salts thereof, where:

X is S, NH, or $N(CH_3)$;

each $R_{N1}$-$R_{N5}$ is independently H or $CH_3$;

$R_1$ is an alkyl group having 1-5 carbon atoms, an optionally substituted phenyl or a benzyl group;

$R_2$ is an optionally substituted phenyl or a benzyl group;

$R_3$ is an alkyl group having 1-6 carbon atoms, a γ-hydroxyalkyl having 1-6 carbon atoms; or a γ-$CONH_2$ substituted alkyl group having 1-6 carbon atoms;

$R_4$ is an alkyl having 1-6 carbon atoms, a γ-hydroxyalkyl group having 1-5 carbon atoms, or an optionally substituted phenyl or a benzyl group;

$R_T$ is an alkyl group having 1-6 carbon atoms, hydrogen, a hydroxyl, or —OR, where R is hydrogen or an alkyl having 1-6 carbon atoms, or $R_T$—CO is an optionally N-methylated peptide ranging in length from 1 to 7 amino acids.

In specific embodiments, $R_T$CO is

P7

P6

P5

P4

P3

-continued

P2

P1 or salts thereof,
where:

each $R_{N6}$-$R_{N12}$ is independently, hydrogen or $CH_3$;

$R_6$ is a straight-chain alkyl having 1-6 carbon atoms or $R_6$ and $R_{N6}$ together with the nitrogen to which $R_{N6}$ is bonded form a 5 or 6 member ring;

$R_7$ is —$(CH_2)_{1-3}$—OH or —$(OH_2)_{1-3}$—$CONH_2$;

$R_8$ is an alkyl group having 1-6 carbon atoms, a γ-COOH substituted alkyl group having 1-6 carbon atoms, a optionally substituted phenyl or an optionally substituted benzyl group;

$R_9$ is an alkyl having 1-3 carbon atoms, hydrogen or a γ-aminoalkyl group having 1-6 carbon atoms;

$R_{10}$ is an alkyl group having 1-3 carbon atoms, or a γ-hydroxyalkyl group having 1-3 carbon atoms;

$R_{11}$ is an alkyl group having 1-3 carbon atoms; and $R_{12}$ is an alkyl group having 1-6 carbon atoms, or a γ-CO—$NH_2$-substituted alkyl group having 1-6 carbon atoms.

In an embodiment, the compounds of formula III exclude AIP-II, AIP-III and G-V-N-A-(C-S-S-L-F) (SEQ ID NO: 9).

In an embodiment, all amino acids of formula III are L-amino acids with the exception that the amino acid with side chain $R_7$ is an L- or a D-amino acid.

In an embodiment of formula III, where $R_T$ is P4:

$R_6$ is an alkyl having 1-3 carbon atoms, preferably methyl;

$R_7$ is a —$(CH_2)_{1-3}$—$CONH_2$, preferably —$CH_2$—$CONH_2$;

$R_8$ is a branched alkyl having 3-5 carbon atoms, preferably iso-propyl, iso-butyl or sec-butyl; and $R_9$ is hydrogen.

In a more specific embodiment of the forgoing embodiment of P4, the macrocycle is of formula B10:

(X10-X11-X12-Y-X14)

where:

X10 is Cys or Dab;

X11 is Ser or Ala;

X12 is Asn or Ala;

X14 is Leu or Phe, or salts or methylated derivatives thereof.

Additional antagonists include among others:

N-A-S-K-Y-N-P(C-A-S-Y-L) (SEQ ID NO: 80), N-A-S-K-Y-N-P(Dab-A-S-Y-L) (SEQ ID NO: 81), N-A-A-K-Y-N-P(C-S-N-Y-L) (SEQ ID NO: 82),

N-A-A-K-Y-N-P(Dab-S-N-Y-L) (SEQ ID NO: 83), or salts or methylated derivatives thereof.

Additional antagonists include among others:

D-S-V-(C-Y-S-Y-F) (SEQ ID NO: 84), D-S-V-(C-S-S-Y-F) (SEQ ID NO: 85), D-S-A-(C-Y-S-Y-F) (SEQ ID NO: 86), D-S-A-(C-S-S-Y-F) (SEQ ID NO: 87),

D-S-A-(C-S-N-Y-L) (SEQ ID NO: 88), D-S-A-(C-A-A-Y-F) (SEQ ID NO: 89), D-S-A-(C-S-A-Y-F) (SEQ ID NO: 90), A-S-A-(C-Y-S-Y-F) (SEQ ID NO: 91),

A-S-A-(C-S-S-Y-F) (SEQ ID NO: 92), A-S-A-(C-S-N-Y-L) (SEQ ID NO: 93), A-S-A-(C-A-A-Y-F) (SEQ ID NO: 94); A-S-A-(C-S-A-Y-F) (SEQ ID NO: 95), (K)a-Y-N-P-(C-Y-S-Y-F) (SEQ ID NO: 96), (K)a-Y-N-P-(C-S-S-Y-F) (SEQ ID NO: 97), (K)a-Y-N-P-(C-S-N-Y-L) (SEQ ID NO: 98), (K)a-Y-N-P-(C-A-A-Y-F) (SEQ ID NO: 99), (K)a-Y-N-P-(C-S-A-Y-F) (SEQ ID NO: 100),

D-S-V-(Dab-Y-S-Y-F) (SEQ ID NO: 101), D-S-V-(Dab-S-S-Y-F) (SEQ ID NO: 102), D-S-A-(Dab-Y-S-Y-F) (SEQ ID NO: 103),

D-S-A-(Dab-S-S-Y-F) (SEQ ID NO: 104), D-S-A-(Dab-S-N-Y-L) (SEQ ID NO: 105), D-S-A-(Dab-A-A-Y-F) (SEQ ID NO: 106),

D-S-A-(Dab-S-A-Y-F) (SEQ ID NO: 107), A-S-A-(Dab-Y-S-Y-F) (SEQ ID NO: 108), A-S-A-(Dab-S-S-Y-F) (SEQ ID NO: 109),

A-S-A-(Dab-S-N-Y-L) (SEQ ID NO: 110), A-S-A-(Dab-A-A-Y-F) (SEQ ID NO: 111); A-S-A-(Dab-S-A-Y-F) (SEQ ID NO: 112), (K)a-Y-N-P-(Dab-Y-S-Y-F) (SEQ ID NO: 113), (K)a-Y-N-P-(Dab-S-S-Y-F) (SEQ ID NO: 114), (K)a-Y-N-P-(Dab-S-N-Y-L) (SEQ ID NO: 115), (K)a-Y-N-P-(Dab-A-A-Y-F) (SEQ ID NO: 116), (K)a-Y-N-P-(Dab-S-A-Y-F) (SEQ ID NO: 117), G-V-N-A-(C-S-N-Y-L) (SEQ ID NO: 118),

G-V-N-A-(C-A-A-Y-F) (SEQ ID NO: 119), G-V-N-A-(C-S-A-Y-F) (SEQ ID NO: 120), G-V-N-A-(Dab-S-N-Y-L) (SEQ ID NO: 121),

G-V-N-A-(Dab-A-A-Y-F) (SEQ ID NO: 122), G-V-N-A-(Dab-S-A-Y-F) (SEQ ID NO: 123) or salts or methylated derivatives thereof, where a is 0 or 1 to show presence of absence of K.

The disclosure provides universal agonists of formula IV:

or salts thereof,
where:

X is S, NH, or $N(CH_3)$;

each $R_{N1}$-$R_{N5}$ is independently hydrogen or methyl;

$R_1$ is a branched alkyl having 3-6 carbons;

$R_2$ is an optionally substituted phenyl or a benzyl group;

$R_3$ is —$(CH_2)_{1-3}$—OH or —$(CH_2)_{1-3}$—$CONH_2$, preferably —$(CH_2)$—OH or —$(CH_2)$—$CONH_2$;

$R_4$ is an alkyl group having 1-3 carbon atoms, or a γ-hydroxyalkyl group having 1-3 carbon atoms;

$R_T$ is P3 or P4:

P4

P3 where:

each $R_{N6}$-$R_{N5}$ is independently hydrogen or methyl, except when $R_6$ together with $R_{N6}$ forms a ring;

$R_6$ is a branched alkyl group having 3-6 carbon atoms, or $R_6$ and $R_{N6}$ together with the nitrogen to which $R_{N6}$ is bonded form a 5 or 6 member heterocyclic ring;

$R_7$ is a straight-chain or branched alkyl group having 3-6 carbon atoms, or is —$(CH_2)_{1-3}$—$CONH_2$, preferably —$(CH_2)$—$CONH_2$;

$R_8$ is an optionally substituted phenyl or benzyl group, and $R_9$ is —$(CH_2)_{3-6}$—$NH_2$, preferably —$(CH_2)_4$—$NH_2$.

In specific embodiments, compounds of formula IV include peptides of formula B20:

(SEQ ID NO: 124)
X9-Y-X7-P-(X5-X4-X3-Y-L), where

X9 is Lys or is absent;

X7 is Asn, Leu or Val;

X5 is Cys or Dab;

X4 is Ala or Ser; and

X3 is Asn or Ser; or salts or methylated derivatives thereof.

In specific embodiments universal agonists are among others:

(K)aYNP(CASYL) (SEQ ID NO: 125), (K)aYNP(CA-NYL) (SEQ ID NO: 126), (K)aYNP(CSSYL) (SEQ ID NO: 127), (K)aYLP(CASYL) (SEQ ID NO: 128), (K)aYLP(CA-NYL) (SEQ ID NO: 129), (K)aYLP(CSSYL) (SEQ ID NO: 130), (K)aYNV(CASYL) (SEQ ID NO: 131), (K)aYNV(CA-NYL) (SEQ ID NO: 132), (K)aYNV(CSSYL) (SEQ ID NO: 133), (K)aYVP(CASYL) (SEQ ID NO: 134), (K)aYVP(CA-NYL) (SEQ ID NO: 135), (K)aYVP(CSSYL) (SEQ ID NO: 136)

(K)aYLP(CSNYL) (SEQ ID NO: 137), (K)aYNV(CS-NYL) (SEQ ID NO: 138), (K)aYVP(CSNYL) (SEQ ID NO: 139), (K)aYNP(DapASYL) (SEQ ID NO: 140), (K)aYNP(DapANYL) (SEQ ID NO: 141), (K)aYNP(DapSSYL) (SEQ ID NO: 142), (K)aYLP(DapASYL) (SEQ ID NO: 143), (K)aYLP(DapANYL) (SEQ ID NO: 144), (K)aYLP(DapSSYL) (SEQ ID NO: 145), (K)aYNV(DapASYL) (SEQ ID NO: 146), (K)aYNV(DapANYL) (SEQ ID NO: 147), (K)aYNV(DapSSYL) (SEQ ID NO: 148), (K)aYVP(DapASYL) (SEQ ID NO: 149), (K)aYVP(DapANYL) (SEQ ID NO: 150), (K)aYVP(DapSSYL) (SEQ ID NO: 151), (K)aYLP(DapSNYL) (SEQ ID NO: 152), (K)aYNV(DapSNYL) (SEQ ID NO: 153), (K)aYVP(DapSNYL) (SEQ ID NO: 154), or salts or methylated derivatives thereof, where a is 0 or 1 to show presence or absence of K and Dap is diamino proprionic acid.

In specific embodiments, compounds of the invention include peptides of formula B25:

(SEQ ID NO: 155)
X9-Y-X7-X6-(X5-X4-X3-Y-L), where

X9 is Lys or is absent;

X7 is Asn, Leu or Val;

X6 is Pro or Val;

X5 is Cys or Dab;

X4 is Ala or Ser; and

X3 is Asn, Ala or Ser; or salts or methylated derivatives thereof.

In specific embodiments, X9 is Lys.

Compounds of formula B25 are exemplified by those of FIGS. 10A-C and 11A-C.

The terms alkyl or alkyl group refer to a monoradical of a straight-chain or branched saturated hydrocarbon. Alkyl groups include straight-chain and branched alkyl groups. Unless otherwise indicated alkyl groups have 1-8 carbon atoms (C1-C8 alkyl groups) and preferred are those that contain 1-6 carbon atoms (C1-C6 alkyl groups) and more preferred are those that contain 1-3 carbon atoms (C1-C3 alkyl groups). Alkyl groups are optionally substituted with one or more non-hydrogen substituents as described herein. Exemplary alkyl groups include methyl, ethyl, n-propyl, iso-propyl, cyclopropyl, n-butyl, s-butyl, t-butyl, n-pentyl, branched-pentyl, n-hexyl, branched hexyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl.

An alkoxy group is an alkyl group, as broadly discussed above, linked to oxygen ($R_{alkyl}$-O—). An alkylthio group is an alkyl group, as broadly discussed above, linked to a sulfur ($R_{alkyl}$-S—). The term amino group is refer to the species —$N(H)_2$—. The term alkylamino refers to the species —NHR" where R" is an alkyl group, particularly an alkyl t bhaving 1-3 carbon atoms. The term dialkylamino refers to the species —$NR"_2$ where each R" is independently an alkyl group, particularly an alkyl group having 1-3 carbon atoms. The term hydroxyalkyl refers to an alkyl group most generally substituted with one or more OH groups. The term includes alkyl groups substituted with one OH group. The term ω-hydroxyl group refers to a straight chain or branched alkyl group with a single OH group on the omega carbon atom (furthest away from the bond of the group to the rest of the molecule). When the alkyl group is branched, the ω-hydroxy group is substituted at the end of the longest branch. When the branches are of equal length only one branch is hydroxylated.

More generally, the term ω-substituted refers to substitution on the omega carbon atom of an alkyl group (furthest away from the bond of the group to the rest of the molecule). When the alkyl group is branched, the ω-substituent group is substituted at the end of the longest branch. When the branches are of equal length, only one branch is substituted.

Groups herein are optionally substituted most generally with one or more alky, alkenyl, alkynyl, and aryl, heteroaryl groups can be substituted with one or more halogen, hydroxyl group, nitro group, cyano group, isocyano group, oxo group, thioxo group, azide group, cyanate group, isocyanate group, acyl group, haloakyl group, alkyl group, alkenyl group or alkynyl group (particularly those having 1-4 carbons), a phenyl or benzyl group (including those that are halogen or alkyl substituted), alkoxy, alkylthio, or mercapto (HS—). In specific embodiments, optional substitution is substitution with 1-12 non-hydrogen substituents. In specific embodiments, optional substitution is substitution with 1-6 non-hydrogen substituents. In specific embodiments, optional substitution is substitution with 1-3 non-hydrogen substituents. In specific embodiments, optional substituents contain 6 or fewer carbon atoms. In specific embodiments, optional substitution is substitution by one or more halogen, hydroxy group, cyano group, oxo group, thioxo group, unsubstituted C1-C6 alkyl group or unsubstituted aryl group. The term oxo group and thioxo group refer to substitution of a carbon atom with a ═O or a ═S to form respectively —CO— (carbonyl) or —CS— (thiocarbonyl) groups.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di , tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the groups herein which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Compounds of the disclosure, particularly compounds of formulas I, II, III and IV, can be prepared by one of ordinary skill in the art in view of the descriptions provided herein and what is known in the art from commercially or otherwise readily available starting materials and reagents. As described herein in the Examples, standard solid-phase methods of peptide synthesis can be readily adapted for synthesis of the compounds of the formulas herein. Methods for insertion of peptoids, and N-methylated amino acids into such compounds are known in the art and can, as described herein, be readily adapted to such preparation. U.S. Pat. No. 9,227,996 is incorporated by reference herein in its entirety for further details of synthesis for additional assay methods or details thereof and for further applications of compounds herein. Each of references 43, and 53-61 are specifically incorporated by reference herein in its entirety for structures of known Modulators of *Staphylococcus* species, said know modulators can be excluded from the claims herein.

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, *Experimental and computational approaches to estimate solubility and permeability in drug discovery and development settings,* Adv. Drug Del. Rev., 2001, 46, 3-26 and Arup K. Ghose, Vellarkad N. Viswanadhan, and John J. Wendoloski, *A Knowledge-Based Approach in Designing Combinatorial or Medicinal Chemistry Libraries for Drug Discovery,* J. Combin. Chem., 1999, 1, 55-68.) In general a preferred drug for oral administration exhibits no more than one violation of the following rules:

(1) Not more than 5 hydrogen bond donors (e.g., nitrogen or oxygen atoms with one or more hydrogens);

(2) Not more than 10 hydrogen bond acceptors (e.g., nitrogen or oxygen atoms);

(3) Molecular weight under 500 g/mol and more preferably between 160 and 480; and (4) log P less than 5 and more preferably between −0.4 to +5.6 and yet more preferably −1<log P<2.

Compounds herein preferred for therapeutic application include those that do not violate one or more of 1-4 above. Compounds herein preferred for therapeutic application include those having log P less than 5 and more preferably between −0.4 to +5.6 and yet more preferably −1<log P.

Compounds herein may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydroabietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Salt of the invention include "pharmaceutically acceptable salts" which refers to those salts which retain the biological effectiveness and properties of the free bases or free acids, and which are not biologically or otherwise undesirable. Pharmaceutically acceptable salts comprise pharmaceutically-acceptable anions and/or cations.

Compounds herein, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

With respect to the various compounds herein, the atoms therein may have various isotopic forms, e.g., isotopes of hydrogen include deuterium and tritium. All isotopic variants of compounds of the invention are included within the invention and particularly included at deuterium and $^{13}C$ isotopic variants. It will be appreciated that such isotopic variants may be useful for carrying out various chemical and biological analyses, investigations of reaction mechanisms and the like. Methods for making isotopic variants are known in the art.

The disclosure expressly includes pharmaceutically usable solvates of compounds according to formulas herein. The compounds of formula I can be solvated, e.g. hydrated. The solvation can occur in the course of the manufacturing process or can take place, e.g. as a consequence of hygroscopic properties of an initially anhydrous compound of formulas herein (hydration).

Compounds herein can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Suitable examples of liquid carriers for oral and parenteral administration include water of appropriate purity, aqueous solutions (particularly containing additives, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form. The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

Staphylococcal infections, particularly S. aureus infections, can affect various parts of the body and can include skin infection and more serious conditions such as osteomyelitis, endocarditis, septic arthritis, and toxic shock syndrome. S. aureus strains are considered the leading cause of nosocomial infections in the United States. Staphylococcal infections, particularly S. aureus infections, caused by a strain that is resistant to commonly used antibiotics are particularly serious and life-threatening. Of particular concern are strains that exhibit increased resistance to vancomycin.

Compounds herein are useful in the treatment of such infections.

Administration of one or more compounds of the invention can be combined with antibiotic regimens used for the treatment of staphylococcal infections. Various known antibiotics and various known antibiotic regimens can be employed in combination with one or more of the compounds of this invention. One of ordinary skill in the art can select form a variety of known antibiotics, which may be used alone or in combination, and which can specifically include, vancomycin, linezolid, and oxacillin. For example, one or more compounds of the invention can be used in combination with intravenous or oral antibiotics.

In another embodiment, the disclosure provides a medicament for treatment of an infectious disease, particularly a staphylococcal infection. The medicament comprises a therapeutically effective amount of one or more compounds of this invention as illustrated in one or more formulas herein which compounds exhibit antivirulence and/or antibacterial activity. In a specific embodiment, the medicament of this invention can also comprise a therapeutically effective amount of one or more antibiotics. The invention also provides a method for making this medicament which comprises combining a therapeutically effective amount of one or more compounds of this invention having antivirulence activity with a selected pharmaceutical carrier appropriate for a given method of administration. In a specific embodiment, the method for making a medicament can additional include combining a therapeutically effective amount of one or more antibiotics in the medicament. The medicament may be an oral dosage form, an intravenous dosage form or any other art-recognized dosage form.

The present disclosure also provides methods of increasing or reducing the virulence of *Staphylococcus* species and specifically *Staphylococcus aureus*. In one aspect, the method comprises contacting a bacterium with an effective amount of a compound of the present invention. In another aspect, the method comprises contacting a bacterium with a therapeutically effective amount of a pharmaceutically acceptable salt of the compounds of the present invention. In yet another aspect, the method comprises contacting a bacterium with a precursor which can form an effective amount of a compound of the present invention.

Methods herein comprise the step of administering a "therapeutically effective amount" of the present therapeutic formulations containing the present compounds, to treat, reduce or regulate a disease state in a patient, including a disease state involving one or more infectious agents such as bacteria. The term "therapeutically effective amount," as used herein, refers to the amount of the therapeutic formulation, that, when administered to the individual is effective to treat, reduce or regulate a disease state in a patient, including a disease state involving one or more infectious agents such as bacteria and more specifically *Staphylococcus*. As is understood in the art, the therapeutically effective amount of a given compound or formulation will depend at least in part upon, the mode of administration (e.g. intravenous, oral, topical administration), any carrier or vehicle employed, and the specific individual to whom the formulation is to be administered (age, weight, condition, sex, etc.). The dosage requirements need to achieve the "therapeutically effective amount" vary with the particular formulations employed, the route of administration, and clinical objectives. Based on the results obtained in standard pharmacological test procedures, projected daily dosages of active compound can be determined as is understood in the art.

Compounds herein are useful in therapeutic methods, particularly for treating infections. Any suitable form of administration can be employed in the method herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts.

Compounds herein can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol. Administration includes any form of administration that is known in the art and is intended to encompass administration in any appropriate dosage form and further is intended to encompass administration of a compound, alone or in a pharmaceutically acceptable carrier. Pharmaceutical carriers are selected as is known in the art based on the chosen route of administration and standard pharmaceutical practice.

Compounds herein can also be administered to the eye, preferably as a topical ophthalmic formulation. The compounds of this invention can also be combined with a preservative and an appropriate vehicle such as mineral oil or liquid lanolin to provide an ophthalmic ointment. The compounds of this invention may be administered rectally or vaginally in the form of a conventional suppository. The compounds of this invention may also be administered transdermally through the use of a transdermal patch containing the active compound and a carrier that is inert to the active compound, is non-toxic to the skin, and allows delivery of the agent for systemic absorption into the blood stream via the skin.

Compounds herein may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

Pharmaceutical compositions and medicaments herein comprise one or more compounds in combination with a pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety. The disclosure also encompasses method for making a medicament employing one or more compounds of this invention which exhibit a therapeutic effect.

In another aspect, the present disclosure provides pharmaceutical and therapeutic preparations comprising a therapeutically effective amount of one or more compounds of the present invention of Formula I optionally in combination with a pharmaceutically acceptable carrier. In particular, pharmaceutical and therapeutic preparations of this invention comprise an amount or combined amount of one or more compounds of this invention effective for bacterial interference, particularly of a *Staphylococcus* species and more particularly of *Staphylococcus epidermidis* or *S. aureus* and more particularly a strain which is a bacterial human or veterinary pathogen. Compounds useful in the methods herein include pharmaceutically-acceptable salts of the compounds of formulas herein. Compounds useful in the methods herein include pharmaceutically-acceptable prodrugs of the compounds of formulas herein. Salts include any salts derived from the acids of the formulas herein which are acceptable for use in human or veterinary applications. Bacterial interference includes attenuation of virulence.

In another aspect, the disclosure provides a method of treating an infectious disease comprising administering to an individual in need of treatment, a composition comprising one or more compounds herein. In an embodiment, the infectious disease relates to that associated with an infectious agent comprising a bacterium. In a specific embodiment, the bacteria are *Staphylococcus*. In a specific embodiment, the bacteria are one or more selected from the group consisting of *S. aureus*, or *S. epidermidis*. In a specific embodiment, the bacteria are one or more drug resistant *Staphylococcus*. Compounds of the invention can be employed in human treatment or in veterinary treatment.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

AIP-I SARs Revealed Through Alanine and D-Amino Acid Scans

Each amino acid of the *S. epidermidis* AIP-I was systematically replaced with either alanine or the corresponding D-amino acid to explore the roles of each side chain and stereocenter in the interaction between AIP-I and AgrC-I, with the exception that Cys4 was not mutated to Ala due to the requirement for macrocycle formation, and Ala5 did not require alanine replacement. The initial set of 14 analogs (listed in Table 1) was synthesized using solid-phase peptide chemistry and purified to homogeneity using previously established HPLC methods (59). Each analog was tested for its ability to modulate the activity of the AgrC-I receptor using a wild-type *S. epidermidis* Group-I fluorescence reporter strain. This strain contained a reporter plasmid encoding a gfp gene fused to the P3 promoter found upstream of RNAIII (36). Under high cell-density conditions, activation of the AgrC-I receptor by the endogenously produced AIP-I leads to phosphorylation of AgrA, which then binds the P3 promoter and activates gfp expression. The level of GFP fluorescence can therefore be quantified as a measurement of the extent of AgrC-I activation (note, this strain then fluoresces in the absence of added AIP-I at high densities). AgrC-I antagonism was measured by testing AIP-I analogs alone, while AgrC-I agonism was measured in the presence of a known strong AgrC-I inhibitor, *S. epidermidis* AIP-II, to block activation of AgrC-I by endogenously produced AIP-I. For comparison, we also evaluated the activities of the native *S. epidermidis* AIPs (I-III) and *S. aureus* AIPs (I-IV), as well as *S. aureus* AIP-III D4A, the most potent pan-group inhibitor of *S. aureus* agr systems that we have reported to date (59). The native AIPs served as important controls for fluorescence reporter assays, as their effects on AgrC-I activation by AIP-I in *S. epidermidis* have been described previously (36, 45); the activity of the lead *S. aureus* agr inhibitor, AIP-III D4A, in *S. epidermidis* was unknown. Compounds demonstrating appreciable antagonism or agonism of AgrC-I in these assays were subjected to dose-response analyses, which permitted calculation of $IC_{50}$ and $EC_{50}$ values. The assay data for the alanine and D-amino acid AIP-I analogs and the control AIPs in AgrC-I are summarized in Table 1.

The activities of the native *S. epidermidis* and *S. aureus* AIPs were congruent with previous reports, with the exception of *S. aureus* AIP-II. *S. aureus* AIP-II was previously reported to be inactive toward *S. epidermidis* AgrC-I (46), but behaved as a relatively strong AgrC-I antagonist in this work. This difference may be attributable to variances in the assay protocol and the strain used (46). Interestingly, *S. aureus* AIP-III D4A, a potent pan-group inhibitor in *S. aureus*, was found to be largely inactive in *S. epidermidis* Group-I, suggesting that this peptide could be used as a species-specific agr inhibitor in *S. aureus*.

Turning to the alanine and D-amino acid scans of AIP-I, several interesting trends in the SAR of the AIP-I:AgrC-I interaction were observed (Table 1). Previous SAR studies of *S. aureus* AIPs have shown that activation of an AgrC receptor by its cognate AIP likely involves two main steps: (i) initial binding of the AIP to AgrC (i.e., AIP "recognition") that is mediated largely by the macrocycle and bulky,

TABLE 1

$IC_{50}$ and $EC_{50}$ values for alanine and D-amino acid scan analogs of *S. epidermidis* AIP-I in AgrC-I determined using a fluorescence reporter strain.[a] Shaded cells represent control peptides.

| Peptide Name | Sequence | SEQ ID NO: | $IC_{50}$ (nM) | $EC_{50}$[b] (nM) |
|---|---|---|---|---|
| AIP-I D1A | A-S-V-(C-A-S-Y-F) | 72 | — | 49.3 |
| AIP-I S2A | D-A-V-(C-A-S-Y-F) | 156 | — | >1000 |
| AIP-I V3A | D-S-A-(C-A-S-Y-F) | 157 | 51.9 | — |
| AIP-I S6A | D-S-V-(C-A-A-Y-F) | 77 | — | 71.0 |
| AIP-I Y7A | D-S-V-(C-A-S-A-F) | 158 | Inactive[c] | |
| AIP-I F8A | D-S-V-(C-A-S-Y-A) | 159 | Inactive[c] | |
| AIP-I D-D1 | DD-S-V-(C-A-S-Y-F) | 160 | — | >1000 |
| AIP-I D-S2 | D-DS-V-(C-A-S-Y-F) | 183 | 192[c] | |
| AIP-I D-V3 | D-S-DV-(C-A-S-Y-F) | 161 | >1000 | — |
| AIP-I D-C4 | D-S-V-(DC-A-S-Y-F) | 162 | Inactive[c] | |
| AIP-I D-A5 | D-S-V-(C-DA-S-Y-F) | 163 | Inactive[c] | |
| AIP-I D-S6 | D-S-V-(C-A-DS-Y-F) | 164 | — | >1000 |
| AIP-I D-Y7 | D-S-V-(C-A-S-DY-F) | 165 | Inactive[c] | |
| AIP-I D-F8 | D-S-V-(C-A-S-Y-DF) | 166 | — | >1000 |
| AIP-I | D-S-V-(C-A-S-Y-F) | 68 | — | 196 |
| AIP-II | N-A-S-K-Y-N-P-(C-S-N-Y-L) | 167 | 9.64 | — |
| AIP-III | N-A-A-K-Y-N-P-(C-A-S-Y-L) | 168 | 34.3 | — |
| *S. aureus* AIP-I | Y-S-T-(C-D-F-I-M) | 8 | Inactive[c] | |
| *S. aureus* AIP-II | G-V-N-A-(C-S-S-L-F) | 9 | 62.9 | — |
| *S. aureus* AIP-III | I-N-(C-D-F-L-L) | 10 | Inactive[c] | |
| *S. aureus* AIP-IV | Y-S-T-(C-Y-F-I-M) | 11 | >1000 | — |
| *S. aureus* AIP-III D4A | I-N-(C-A-F-L-L) | 7 | Inactive[c] | |

[a]See Methods for details of the reporter strain and assay procedures. See Supplementary Information for peptide MS and HPLC characterization data, dose response curves, and 95% confidence intervals (CI) for $IC_{50}$ and $EC_{50}$ values.
[b]Activation dose response curves were performed in the presence of 50 nM *S. epidermidis* AIP-II (an inhibitor) to block activation of AgrC-I by endogenously produced AIP-I.
[c]Dose response curves revealed neither agonism nor antagonism over the concentration range tested.
[d]Maximum inhibition did not exceed 60%.

hydrophobic endocyclic residues, and (ii) subsequent activation of AgrC via interactions with the exocyclic tail region of the bound AIP (55, 61, 63). Consistent with these previous studies, replacement of either of the two hydrophobic residues (Tyr7 and Phe8) in the macrocycle of the *S. epidermidis* AIP-I with alanine resulted in a complete loss of activity in AgrC-I. Furthermore, the substitution of Tyr7 with the corresponding D-amino acid (i.e., AIP-I D-Y7) also caused a complete loss of activity, demonstrating the stringent requirement of this residue for AIP-I recognition by AgrC-I. AIP-I D-F8, however, maintained agonistic activity, albeit with lower potency relative to AIP-I, suggesting that the spatial configuration at this position plays less of a role in AIP-I:AgrC-I interactions in comparison to the composition of the side chain. Also in agreement with prior observations of AgrC receptor activation by receptor bound AIPs (16, 55), alanine or D-amino acid replacements at residue Val3 in the exocyclic tail region converted AIP-I into a moderate or weak antagonist, respectively, demonstrating that Val3 likely plays an important role in AgrC-I activation. Replacing the nearby residue Ser2 with an alanine caused a decrease in agonistic activity, indicating that Ser2 contributes to AgrC-I activation by AIP-I. In addition, substitution with the D-amino acid counterpart at Ser2 yielded a weak AgrC-I antagonist, suggesting that the orientation of the residue at this position may influence the presentation of the key activating residue, Val3.

Converting both Cys4 and Ala5 residues to their D-isomers caused a complete loss of activity. Given the locations of these two stereocenters relative to the key thioester linkage forming the macrocycle, this loss of activity could be the result of either a stringent requirement for the correct local stereochemistry at these two positions for AIP-I recognition or a global shift in the macrocycle conformation that prevents proper interaction between the key hydrophobic residues and AgrC-I. Additional structural studies are needed to provide a more definitive explanation for these observed effects. Perhaps the most intriguing finding in these initial AIP-I scans was that substitution of either Asp1 in the exocyclic tail or Ser6 in the macrocycle with alanine increased the agonistic activity of AIP-I on AgrC-I (by 2-4-fold). This observation is the first report that two residues in a native AIP allow for suboptimal activation of its cognate AgrC receptor. Previous SAR studies in *S. aureus* have identified only one residue in a single native AIP (*S. aureus* AIP-II) where a mutation yielded an analog with an increased agonistic activity relative to the starting structure (the extent of this increase was not reported) (16). Replacement of Asp1 and Ser6 with their D-Amino acid counterparts reduced, but did not abolish, the agonistic activity of AIP-I. Together, these SAR trends suggest that the spatial configuration of these two residues contribute to the productive binding of AIP-I to its receptor, while the side chain composition of these residues appear to hinder optimal AIP-I:AgrC-I interactions (relative to alanine analogs).

Example 2

SAR Studies Direct the Design of Second-Generation AIP-I Analogs

A second set of *S. epidermidis* AIP-I analogs was designed and synthesized to further examine the SAR trends revealed by the alanine and D-Amino acid analogs, and to potentially generate more potent modulators of AgrC-I. This set of analogs included peptides with substitutions at Ala5 (a position inaccessible through the alanine scan), combinatorial alanine modifications, and truncations to the exocyclic tail. In addition, a series of *S. epidermidis* AIP-II analogs with decreasing length of the exocyclic tail were also synthesized. These latter peptides were designed to explore the use of the AIP-II scaffold for AgrC-I inhibition, as the native AIP-II demonstrated the strongest inhibitory potency of our first-generation analogs and control peptides (see Table 1). The structures of the second-generation analogs are shown in Table 2, and their associated activities in *S. epidermidis* AgrC-I were assessed using the fluorescence reporter assay.

TABLE 2

IC$_{50}$ and EC$_{50}$ values of second-generation AIP analogs in *S. epidermidis* AgrC-I determined using a fluorescence reporter strain.[a]

| Peptide Name | Sequence | SEQ ID NO: | IC$_{50}$ (nM) | EC$_{50}$[b] (nM) |
|---|---|---|---|---|
| AIP-I A5Y | D-S-V-(C-Y-S-Y-F) | 84 | 95.4 | — |
| AIP-I A5S | D-S-V-(C-S-S-Y-F) | 85 | 135[c,d] | |
| AIP-I V3AA5Y | D-S-A-(C-Y-S-Y-F) | 86 | 59.6 | — |
| AIP-I V3AA5S | D-S-A-(C-S-S-Y-F) | 87 | 29.4 | — |
| AIP-I D1AS6A | A-S-V-(C-A-A-Y-F) | 69 | — | 10.3 |
| tAIP-I | Ac-(C-A-S-Y-F) | 169 | 192 | — |
| AIP-I D1AS6AV3A | A-S-A-(C-A-A-Y-F) | 94 | 2.84 | — |
| AIP-I D1AS6AV3AA5S | A-S-A-(C-S-A-Y-F) | 95 | 2.08 | — |
| AIP-II 11aa | A-S-K-Y-N-P-(C-S-N-Y-L) | 170 | 5.43 | — |
| AIP-II 10aa | S-K-Y-N-P-(C-S-N-Y-L) | 171 | 5.29 | — |
| AIP-II 9aa | K-Y-N-P-(C-S-N-Y-L) | 172 | 2.83 | — |
| AIP-II 8aa | Y-N-P-(C-S-N-Y-L) | 173 | 6.08 | — |

TABLE 2-continued

IC$_{50}$ and EC$_{50}$ values of second-generation AIP analogs in *S. epidermidis* AgrC-I determined using a fluorescence reporter strain.[a]

| Peptide Name | Sequence | SEQ ID NO: | IC$_{50}$ (nM) | EC$_{50}$[b] (nM) |
|---|---|---|---|---|
| AIP-II 7aa | N-P-(C-S-N-Y-L) | 174 | 721 | — |
| tAIP-II | Ac-(C-S-N-Y-L) | 175 | >1000 | — |

[a,b]footnotes in Table 1.
[c]Maximum inhibition did not exceed 75%.
[d]Two different AIP-I A5S analogs were isolated that exhibited differing activities; IC$_{50}$ value listed is derived from the antagonism dose response curves for A5S-1 (see text).

To assess the role of the Ala5 side chain in the AIP-I: AgrC-I interaction, Ala5 was replaced with either serine or tyrosine. These modifications were selected based on the primary structures of the native *S. aureus* and *S. epidermidis* AIPs that were found to exhibit inhibitory activities against AgrC-I (Table 1). Specifically, with the exception of *S. epidermidis* AIP-III having an alanine, all other native AIPs active in AgrC-I possess either a serine or a tyrosine at the second endocyclic position. Substitution of Ala5 with a tyrosine yielded a weak AgrC-I antagonist (Table 2), whereas substitution with a serine surprisingly produced two peptide products of the correct mass with differing activities (A5S-1 and A5S-2). Analog A5S-1 behaved as a weak inhibitor against AgrC-I, while A5S-2 displayed a non-monotonic dose response that indicated very weak inhibition at low concentrations yet activation at higher concentrations. When either the A5Y or A5S modification was combined with the inhibitory modification V3A, the resulting analogs, AIP-I V3AA5Y and AIP-I V3AA5S, exhibited similar inhibitory activities as the parent compound AIP-I V3A. One possible explanation for these observations is that the modifications at Ala5 influence the orientation of the activating residue Val3, leading to varying degrees of AgrC-I activation. When the activating valine is replaced with an alanine, the mutations of Ala5 have little to no effect on the activity of the resulting analogs. The chemical difference between the two AIP-I A5S analogs remains unclear.

Additional AIP-I analogs were tested with multiple alanine modifications to examine whether their modulatory effects on AgrC-I could be additive. Replacing both Asp1 and Ser6 residues with alanine generated an analog with enhanced agonistic activity in AgrC-I relative to the parent single alanine mutants (Table 2). This observation led to testing the hypothesis that introduction of the inhibitory modification V3A to the D1AS6A analog, an AIP-I analog that presumably associates strongly with AgrC-I, could produce an AgrC-I antagonist with increased potency. Indeed, the resulting analog—AIP-I D1AS6AV3A—was one of the most potent AgrC-I antagonists identified in this study (IC$_{50}$=~2 nM). A similar analog AIP-I D1AS6AV3AA5S, which contained an additional mutation (A5S) that could potentially further enhance AgrC-I binding, exhibited analogous potency as the parent triple mutant. Overall, the activities of these AIP-I analogs with combinatorial alanine mutations strengthened the SAR trends delineated in our first set of AIP-I analogs. Specifically, their activities confirmed that Val3 is the essential residue for activation of AgrC-I and that the side chains of residues Asp1 and Ser6 play a negative role in the AIP-I:AgrC-I interaction. The importance of the exocyclic tail portion of AIP-I (which includes Val3) for AgrC-I activation was further confirmed by the weak inhibitory activity observed for the truncated analog of AIP-I (tAIP-I, Table 2). This observation was again consistent with prior SAR studies in *S. aureus*, where AIP macrocycles without exocyclic tails were shown to be sufficient for receptor recognition but not receptor activation, and thus acted as competitive AgrC inhibitors (16, 55, 64).

AIP-II analogs with varying lengths of the exocyclic tail (Table 2) were examined. Notably, both the native *S. epidermidis* AIP-II and AIP-III signals have markedly longer exocyclic tails relative to other structurally characterized AIPs, and understanding the role of this structural feature, for receptor activation or inhibition, is of fundamental interest (36). The AIP-II analogs in this study were designed to determine whether the primary structure of AIP-II could be reduced, while maintaining the high potency of its inhibitory activity toward AgrC-I. Removing one amino acid at a time from the N-terminus of AIP-II (Table 2, Rows 9-13), it was found that an AIP-II analog with only three amino acids left in the exocyclic tail (AIP-II 8aa) still exhibited inhibitory activity toward AgrC-I with potency similar to the parent AIP-II. Further removal of amino acids from the N-terminus (as in AIP-II 7aa and tAIP-II) caused a dramatic reduction in inhibitory activity. Since AIP-II 8aa has the same number of residues as the most potent AIP-I analogs introduced above, optimization of this AIP-II scaffold using the SAR trends uncovered herein could yield interesting AgrC-I modulators exhibiting strong activities.

Example 3

Agr Group-Selective Inhibition in *S. epidermidis* by Certain AIP Analogs

Figure 2A:
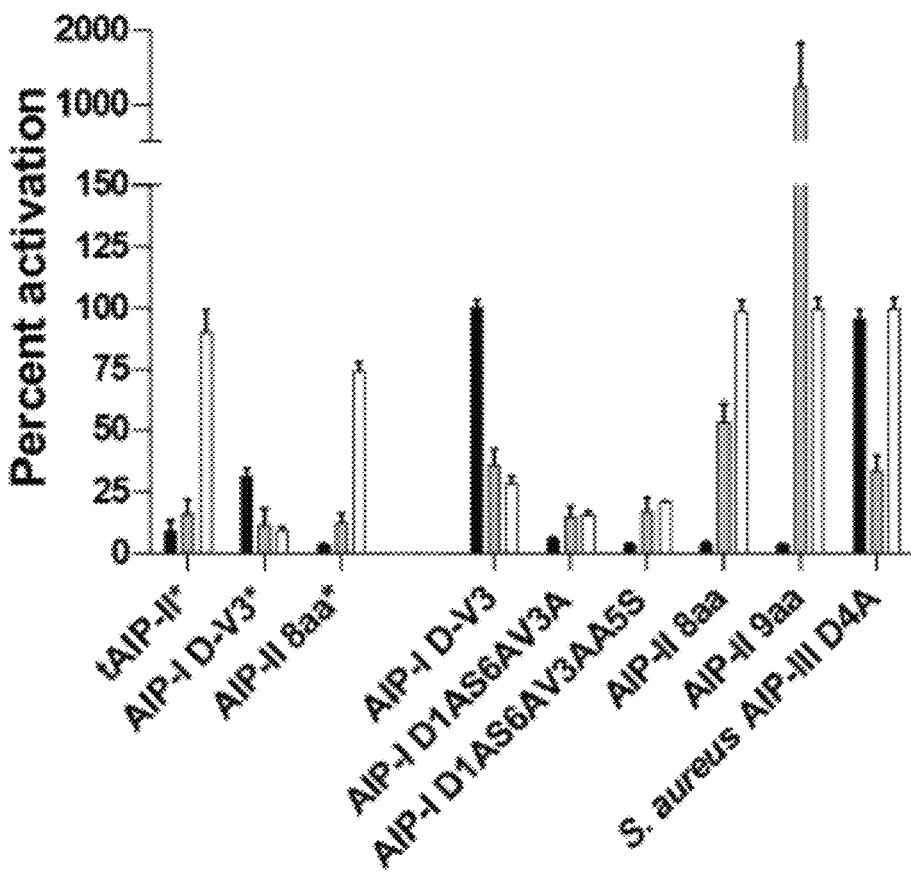
FIGS. 2A and 2B illustrate pan-group activity profiles of selected *S. epidermidis* AIP-I analogs in *S. epidermidis*.
Figure 7A:
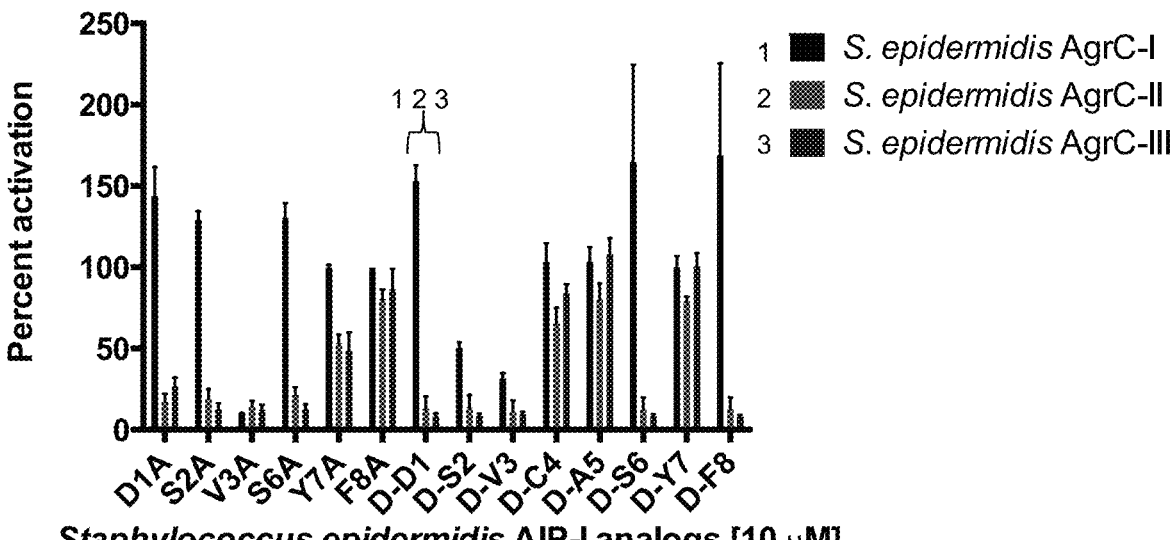
FIGS. 7A-7D are graphs of the effect of certain analogs at 10 microM (unless otherwise indicated) on receptors as indicated as determined using fluorescence reporter strains. Error bars represent the standard deviation of measurements from three biological replicates. See Examples for details of the reporter strains and assay procedures.
Figures 7B, 7C:
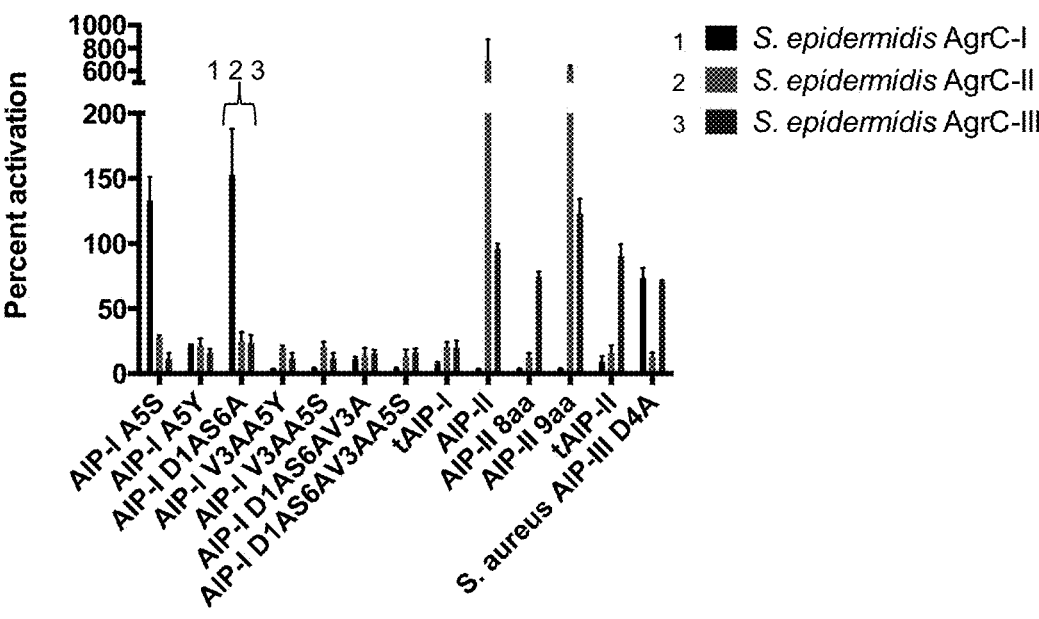

As shown in Table 1, the native AIP-II and AIP-III signals of *S. epidermidis* both inhibit AgrC-I, congruent with the results of Olson et al. (36). However, the biological significance of this agr interference remains unclear, although it has been hypothesized to potentially play a role in competition between different groups in a mixed bacteria milieu (18). Developing chemical modulators that target a specific agr group and are inactive toward the others could provide valuable tools for investigating the hypothesis of agr interference. To this end, the AIP analogs discussed above were screened in GFP reporter strains of Groups-II and -III *S. epidermidis* to complement the Group-I *S. epidermidis* data in Tables 1 and 2 (see Methods; FIGS. 7A and 7B). The only AIP-I analog to show moderate group selectivity was AIP-I Y7A, which was inactive against Group-I, but inhibited AgrC-II and -III to ~50% (FIGS. 7A and &B). More interestingly, two AIP-II analogs, tAIP-II and AIP-II 8aa, were shown to be strongly selective against Group-I and -II at 10 μM (inhibiting to ~75%) but were inactive against Group-III (FIG. 2A).

A subset of peptides was screened in these cross-group screens at a lower concentration to better gauge their relative activities (1 µM or 100 nM; FIG. 2A, FIG. 7C). At the lower concentration, AIP-I D-V3 remained an antagonist against Group-II and Group-III, but lost its inhibitory activity toward Group-I (FIG. 2A). Conversely, AIP-II 8aa remained active toward Group-I at 100 nM, whereas its inhibitory activity against Group-II decreased, making the activity of this analog more Group-I specific. AIP-II 9aa and *S. aureus* AIP-III D4A also exhibited group-selective activities, with AIP-II 9aa being inactive toward Group-III and *S. aureus* AIP-III D4A inhibiting exclusively Group-II. AIP-II 9aa only inhibited Group-I, AIP-II 9aa was also a highly active agonist for Group-II. These selectively profiles are significant, as few agr group selective probes have been reported in any Staphylococcal species (60), and none have been reported in *S. epidermidis*. Accordingly, these peptides represent a valuable new suite of chemical probes, and hold promise for examining the role of agr-based QS competition between any two agr-groups of *S. epidermidis* grown together. For example, by using AIP-II 8aa to target Group-I, *S. aureus* AIP-III D4A to target Group-II, or AIP-I D-V3 to target Group-III, a single agr system can be selectively inhibited in a bacterial population containing two different specificity groups. Additional experiment and discussion of selectivity of peptides as antagonist and agonists is found in Example 7.

Example 4

Potent Pan-Group Inhibitors of the agr System in *S. epidermidis*

Figure 2B:
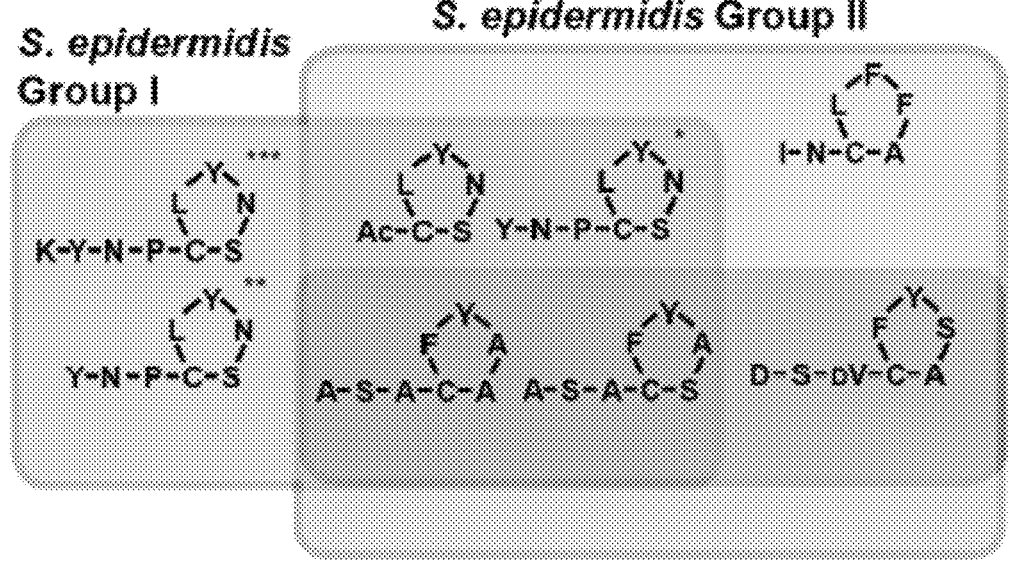
Figure 3A:
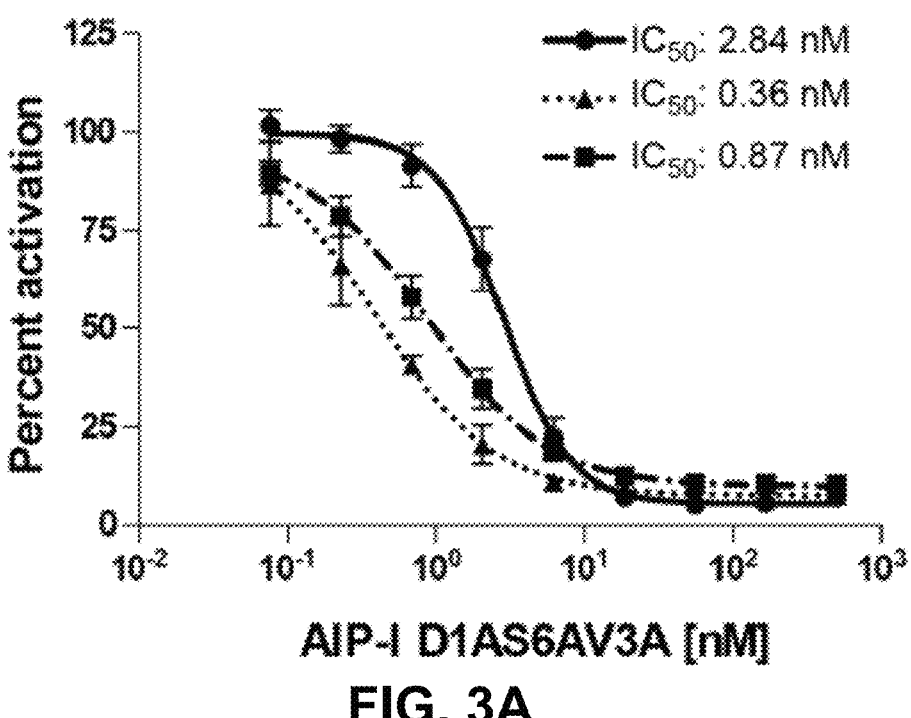
FIGS. 3A and 3B are AgrC antagonism dose response curves and IC$_{50}$ values for (FIG. 3A) AIP-I D1AS6AV3A and (FIG. 3B) AIP-I D1AS6AV3AA5S in the *S. epidermidis* Group-I-III GFP reporter strains. Solid line: Group-I; dotted line: Group-II; dashed line: Group-III. See Methods for strains and assay procedures.
Figure 3B:
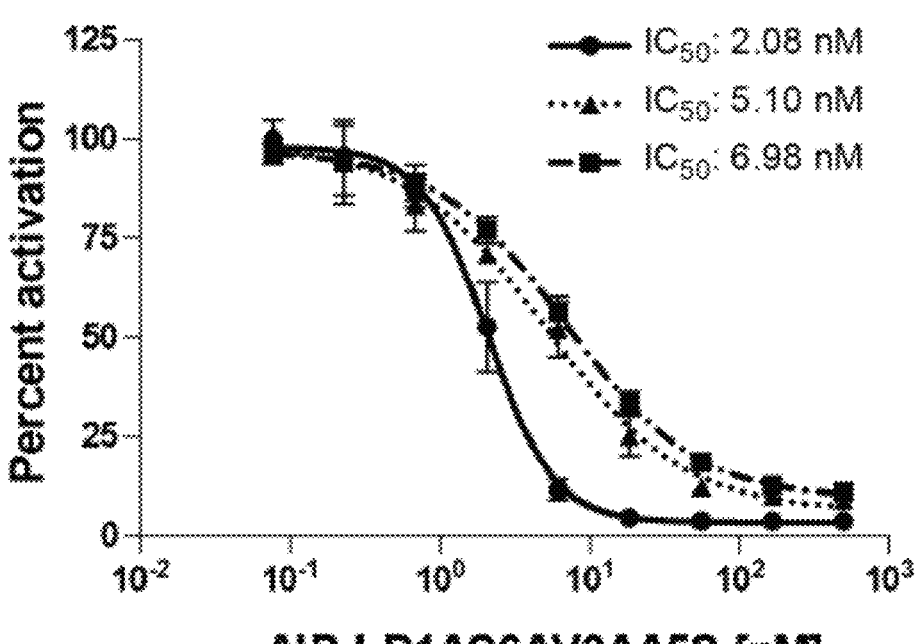

During the efforts to identify agr-group selective modulators, it was noted that AIP-I D1AS6AV3A and AIP-I D1AS6AV3AA5S, two of the most potent inhibitors identified in AgrC-I, also strongly inhibited AgrC-II and AgrC-III at 100 nM (FIGS. 2A and 2B). To determine whether these two analogs were equally potent against AgrC-II and -III, dose response antagonism assays on these analogs were performed. The $IC_{50}$ values obtained for AIP-I D1AS6AV3A and AIP-I D1AS6AV3AA5S against AgrC-II and -III were both in the subnanomolar to low nanomolar range and comparable to their $IC_{50}$ values in AgrC-I (FIGS. 3A and 3B). These two analogs are believed to represent the first potent pan-group inhibitors of the agr system in *S. epidermidis*. Complementary to the selective probes described above, AIP-I D1AS6AV3A and AIP-I D1AS6AV3AA5S should prove useful in a range of fundamental and applied studies, perhaps most useful in applications where agr inhibition in all three groups of *S. epidermidis* is required.

Example 5

AIP Analogs Capable of Species-Specific Inhibition between *S. epidermidis* Group-I and *S. aureus* Groups-I-IV The *S. epidermidis* AIP-I is also known to inhibit the agr system in *S. aureus*. Similar to the cross-group inhibition observed between different agr groups of the same species, this cross-species inhibitory effect has no known biological role, but is hypothesized to provide a competitive advantage on a host (18, 46). Thus, AIP analogs described herein were examined to identify potential species-specific inhibitors that target either *S. epidermidis* Group-I or *S. aureus*

Figure 4:
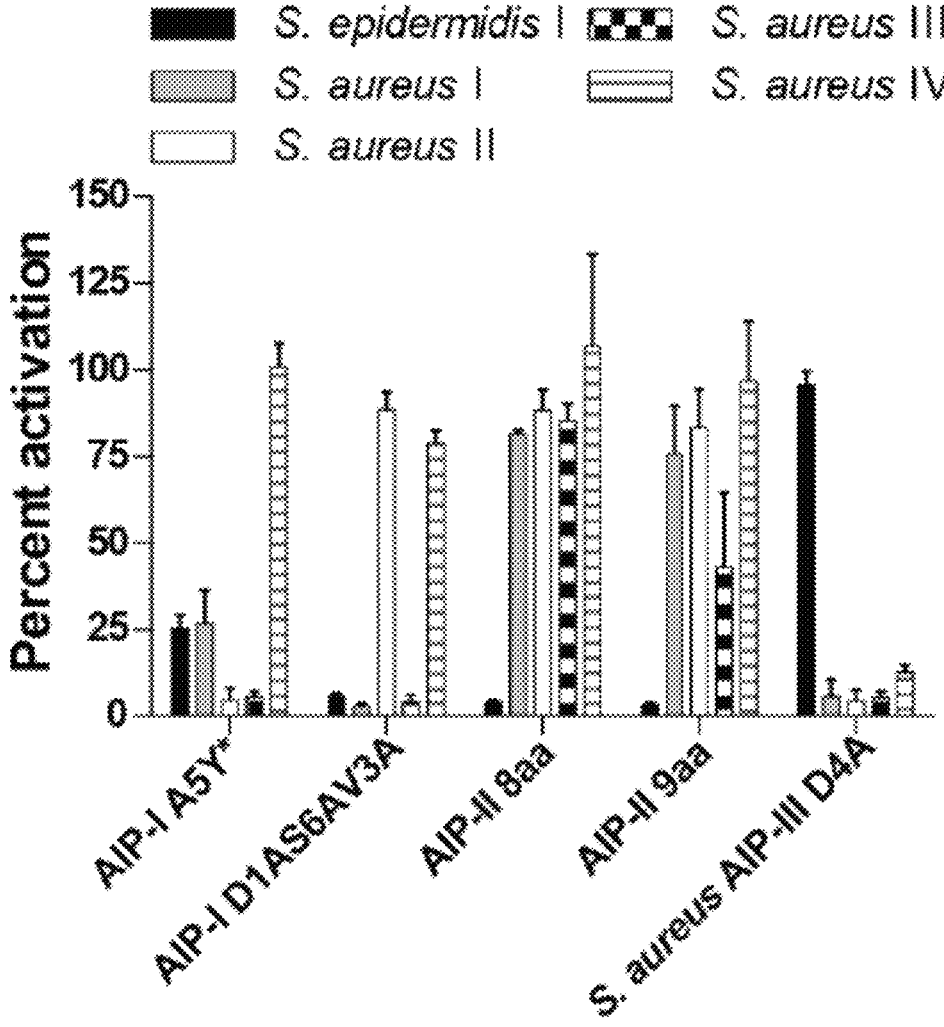
FIG. 4 is a graph illustrating the effects of selected AIP analogs on the AgrC-I receptor in *S. epidermidis* Group-I and the AgrC I-IV receptors in *S. aureus* Groups-I-IV. Compounds tested at 100 nM unless otherwise noted. * Compound tested at 1 µM. See Methods for details of strains and assay procedures.
Figure 7D:
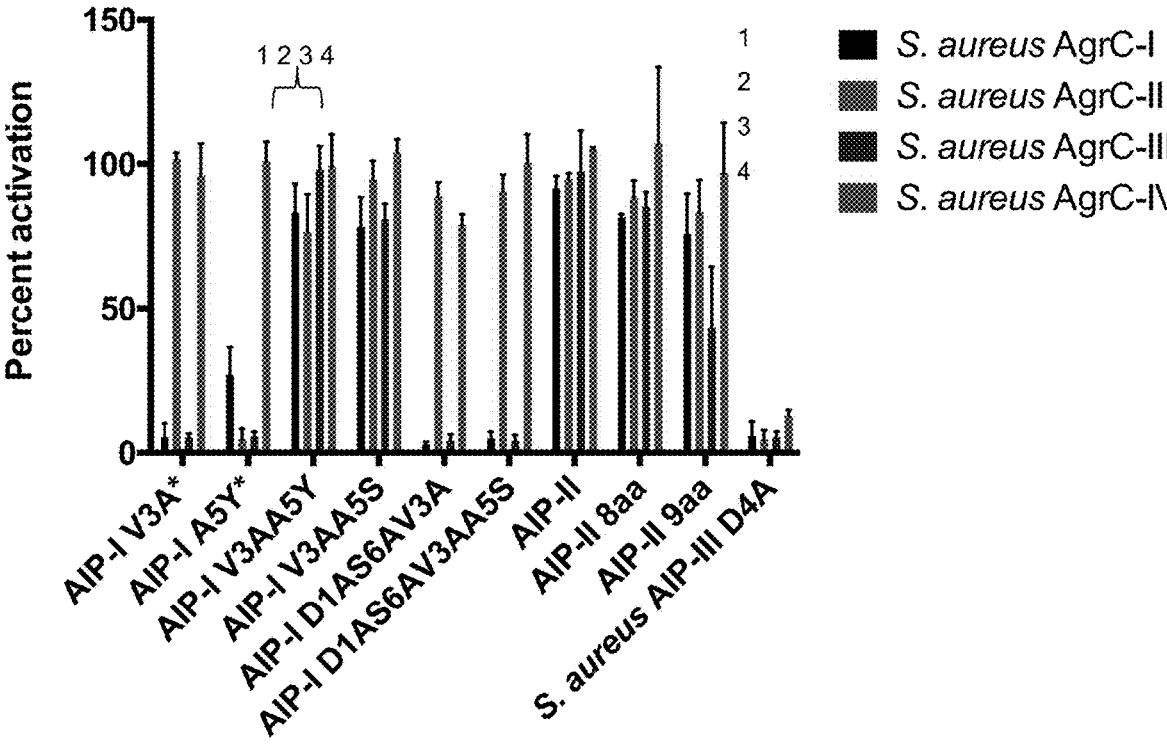
Figure 8A:
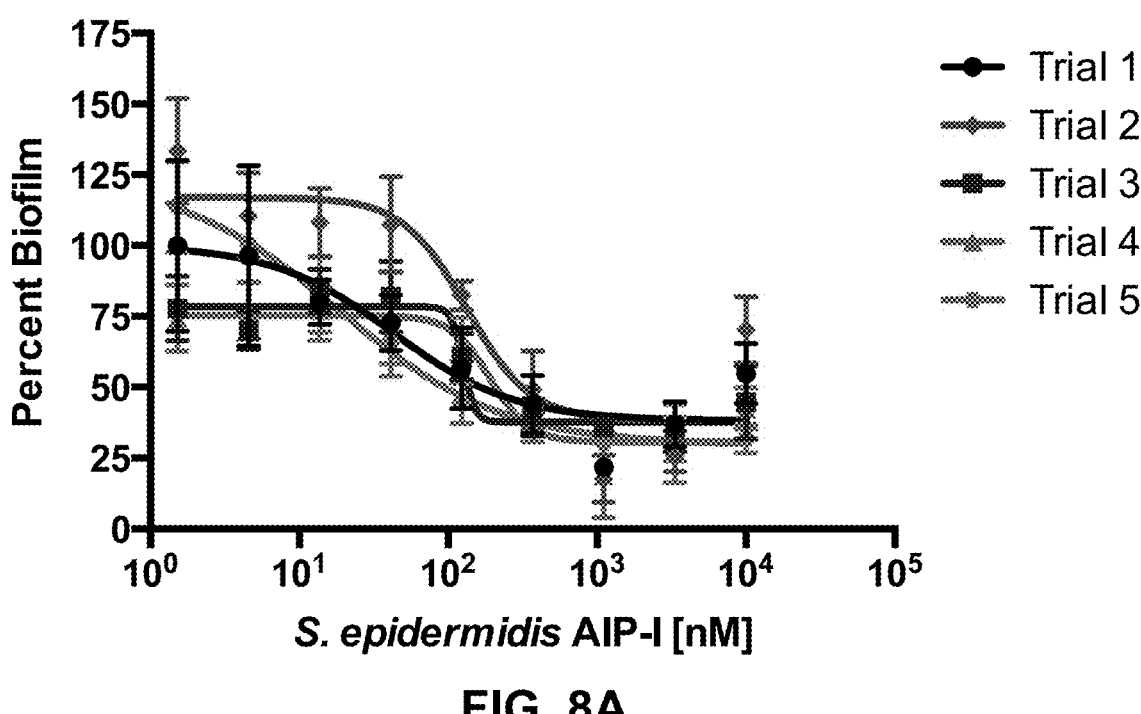
FIGS. 8A and 8B show S. epidermidis biofilm growth inhibition dose response curves for (FIG. 8A) AIP-I and (FIG. 8B) AIP-I D1AS6A. Peptides were screened over varying concentrations in (wild-type) S. epidermidis Group-I RP62A after 24 h in at least four separate experiments. Biofilm growth was measured by staining with crystal violet (CV). Error bars represent the standard deviation of triplicate values from each experiment. Percent activation was normalized to a DMSO control. See main text for details of the strain and assay procedure.
Figure 8B:
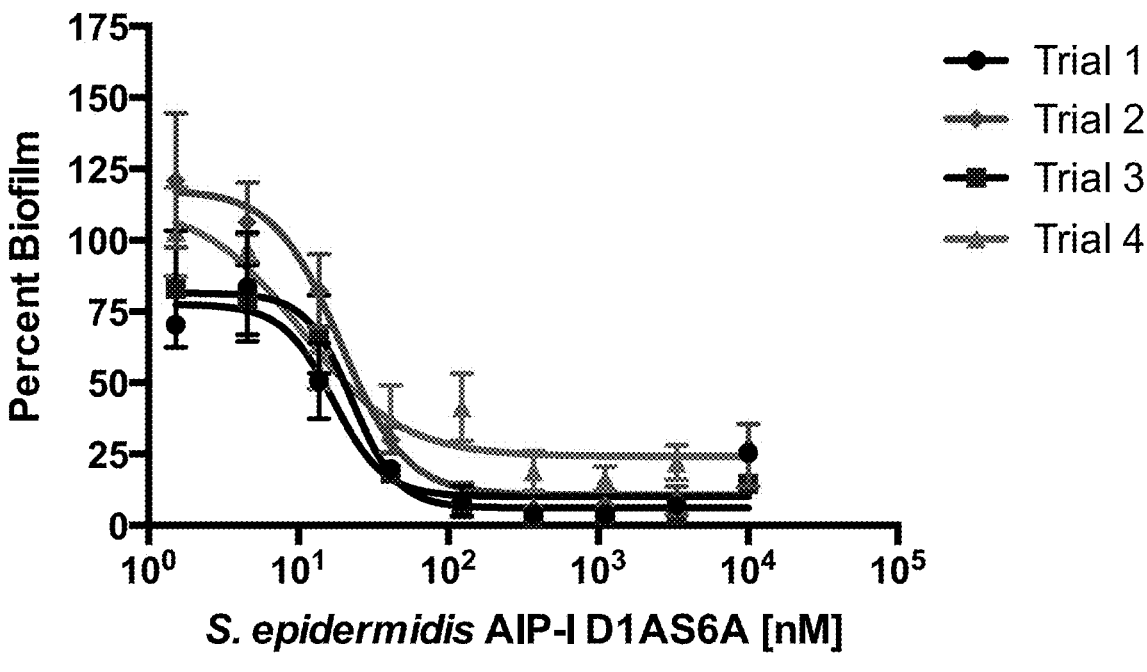

Groups-I-IV. As noted in the discussions above, *S. aureus* AIP-III D4A, a potent pan-group inhibitor against *S. aureus*, was inactive against *S. epidermidis* Group-I at 100 nM (FIG. 4). All of the AIP analogs reported herein capable of inhibiting the agr system in *S. epidermidis* Group-I were screened for activity against the agr systems of *S. aureus* Groups-I-IV using analogous GFP reporter constructs (see Methods). Three peptides were identified (FIG. 4 and FIG. 7D), chief among them AIP-II 8aa, that selectively inhibited the agr system in *S. epidermidis* Group-I without significantly affecting agr activity in *S. aureus* Groups-I-IV. Another analog, AIP-II 9aa, was shown to be largely an inhibitor specific to *S. epidermidis* Group-I, with only weak inhibitory activity in *S. aureus* Group-III. These two analogs, together with *S. aureus* AIP-III D4A, represent the first set of species-specific, chemical modulators targeting the agr systems of either *S. epidermidis* or *S. aureus*.

Example 6

Figure 5:
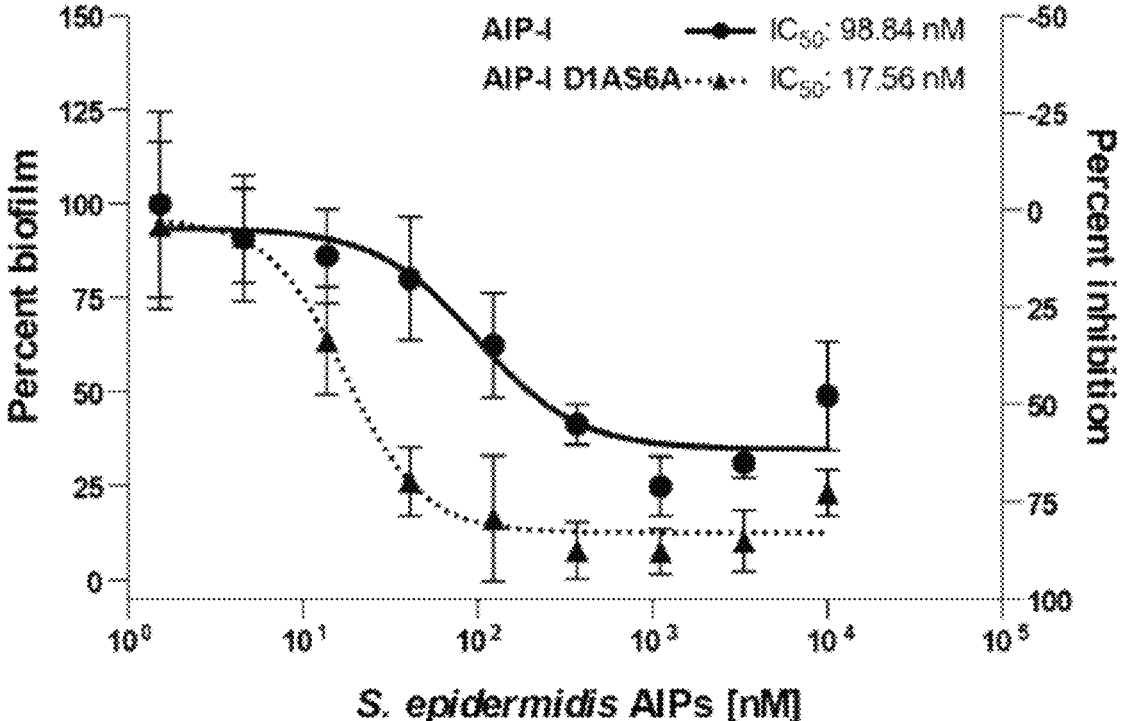
FIG. 5 illustrates (Top) biofilm antagonism dose response curves for *S. epidermidis* AIP-I (closed circles) and AIP-I D1AS6A (closed triangles) against *S. epidermidis* Group-I RP62A strain as determined by CV staining (see Methods for assay procedure). Dose response curves shown represent the average of at least 4 biological replicates. (Bottom) representative image of the CV assay with *S. epidermidis* AIP-I and AIP-I D1AS6A over a range of concentrations. Blue color (dark color) correlates with biofilm growth.
Figure 5:
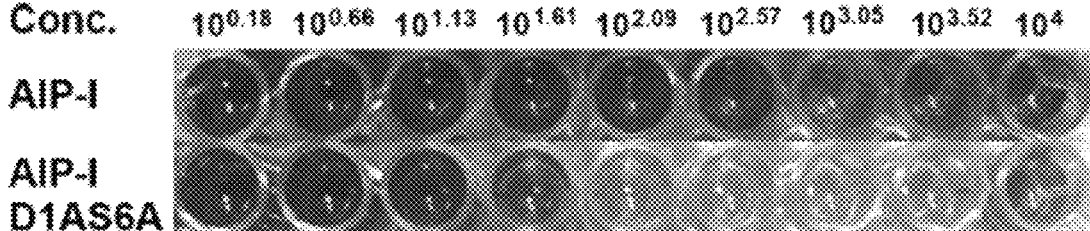

Modulation of Biofilm Formation in *S. epidermidis* Group-I Using Non-Native AIPs As described above, the use of fluorescence reporter strains allowed for the rapid screening of AIP analogs and the identification of AgrC modulators with varying activities. However, the responses from an artificial reporter gene system may not translate to effects on relevant QS phenotypes. As a validation for the physiological relevance of the new AgrC modulators uncovered in this study, the ability of select non-native AIPs to modulate biofilm formation by *S. epidermidis* Group-I was assessed using the PIA-producing strain RP62A in a crystal violet (CV) static biofilm assay (see Methods). Again, biofilm formation is the most important virulence phenotype associated with infection by *S. epidermidis*, and previous reports have established that its agr system plays an important role in biofilm formation (see above) (10, 35). In particular, activation of the agr system is believed to disperse biofilm, thereby preventing the accumulation of sessile bacteria on a surface. Addition of native AIP-I (an AgrC agonist) was found to inhibit *S. epidermidis* biofilm growth, in agreement with a similar study in *S. aureus* (32). Static biofilm assays in 96-well microtiter plates in the presence of exogenous AIP-I showed substantial biofilm reduction (by ~60%, $IC_{50}$=99 nM; FIG. 5). AIP-I D1AS6A, the AIP-I analog identified with enhanced agonistic activity in AgrC-I relative to AIP-I, was tested for modulation of *S. epidermidis* biofilm formation, and in agreement with its effect on the fluorescent reporter strain, this analog also decreased biofilm formation under similar conditions. In fact, AIP-1 D1AS6A had overall enhanced efficacy and potency relative to AIP-I (~80% inhibition, $IC_{50}$=18 nM; FIG. 5). These matching activity trends provide support for the use of fluorescent reporter strains in identifying *S. epidermidis* AgrC modulators with physiological relevance. Moreover, the results with AIP-I D1AS6A are believed to provide the first non-native AIP analog that can strongly inhibit *S. epidermidis* biofilm growth.

Figure 9:
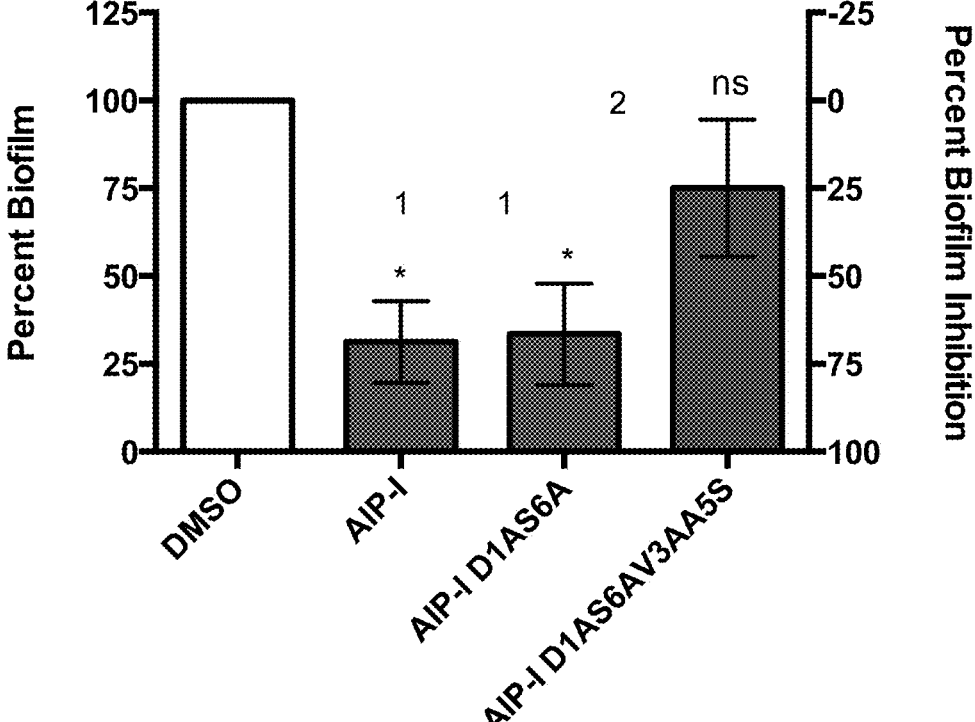
FIG. 9 illustrates single-concentration S. epidermidis biofilm growth inhibition assay data. Selected peptides were tested for effects on biofilm formation in (wild-type) S. epidermidis Group-I RP62A at 10 μM after 24 h. 1:AgrC-I agonist; 2: AgrC-I antagonist. Biofilm growth was measured by staining with crystal violet (CV). Data shown represent the average and the standard deviation of three biological replicates. P-values were calculated using an unpaired t-test compared to a no-peptide DMSO control. *=P<0.05; ns=not significant. See main text for details of the strain and assay procedure.
Figure 10A:
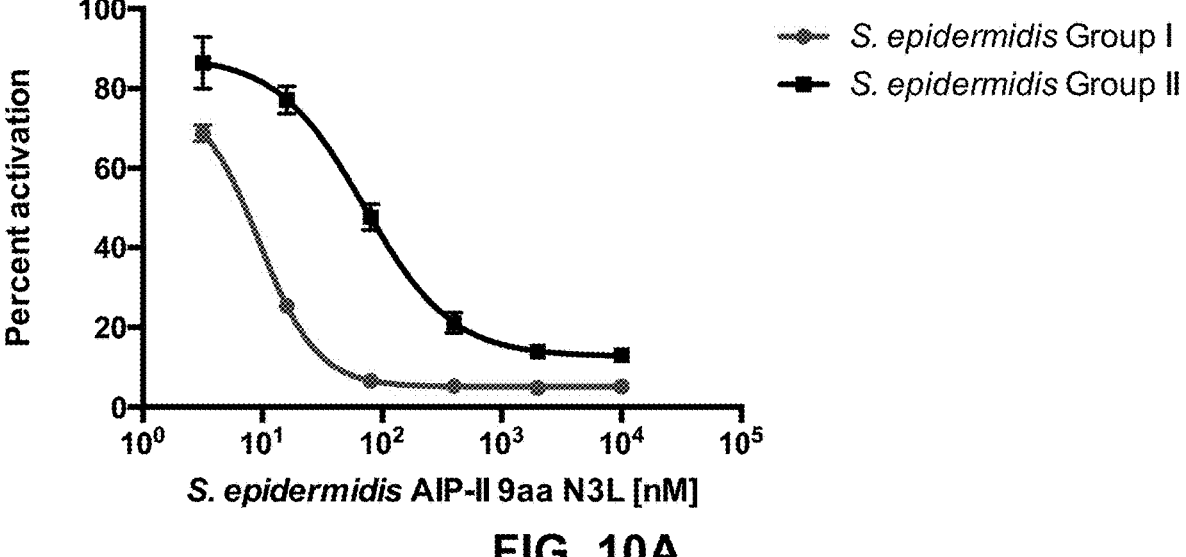
FIGS. 10A, 10B and 10C are single replicate dose response curves for antagonism or agonism as indicated.
Figure 10B:
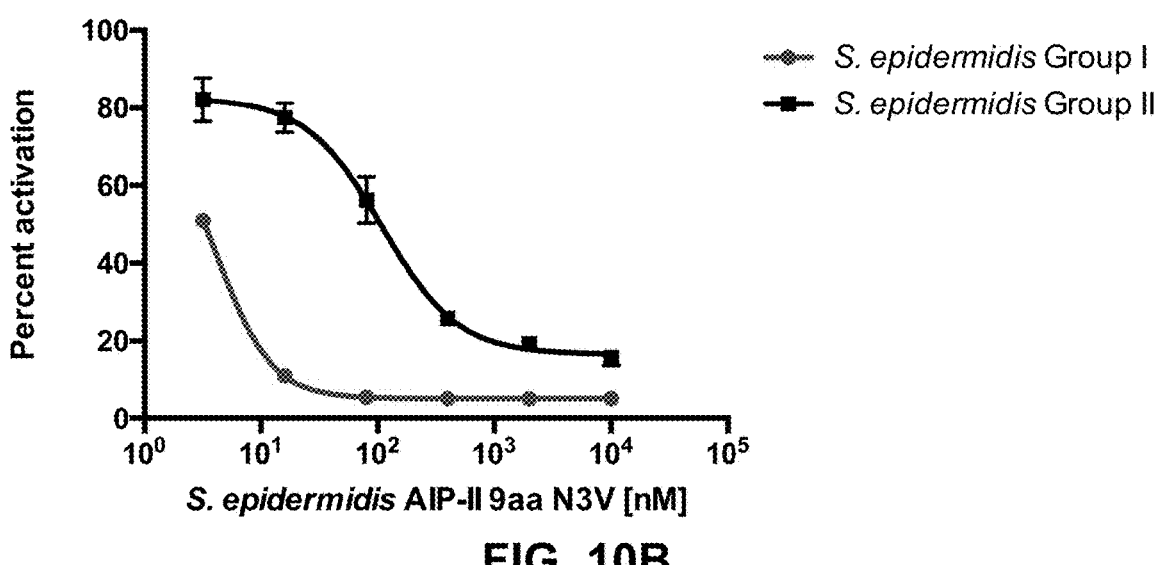
Figure 10C:
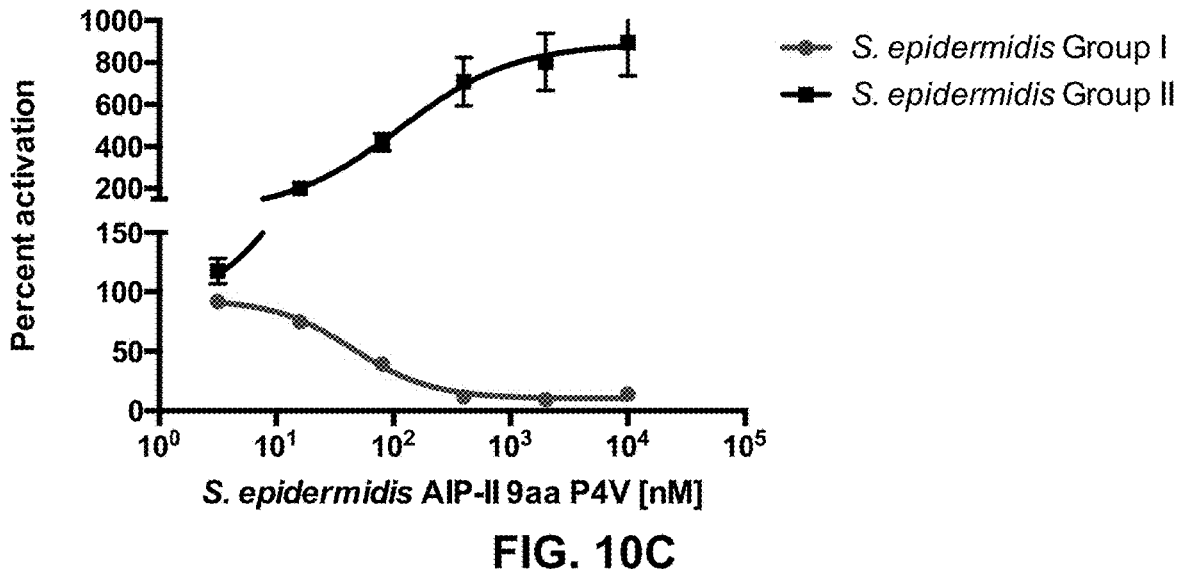
Figure 11A:
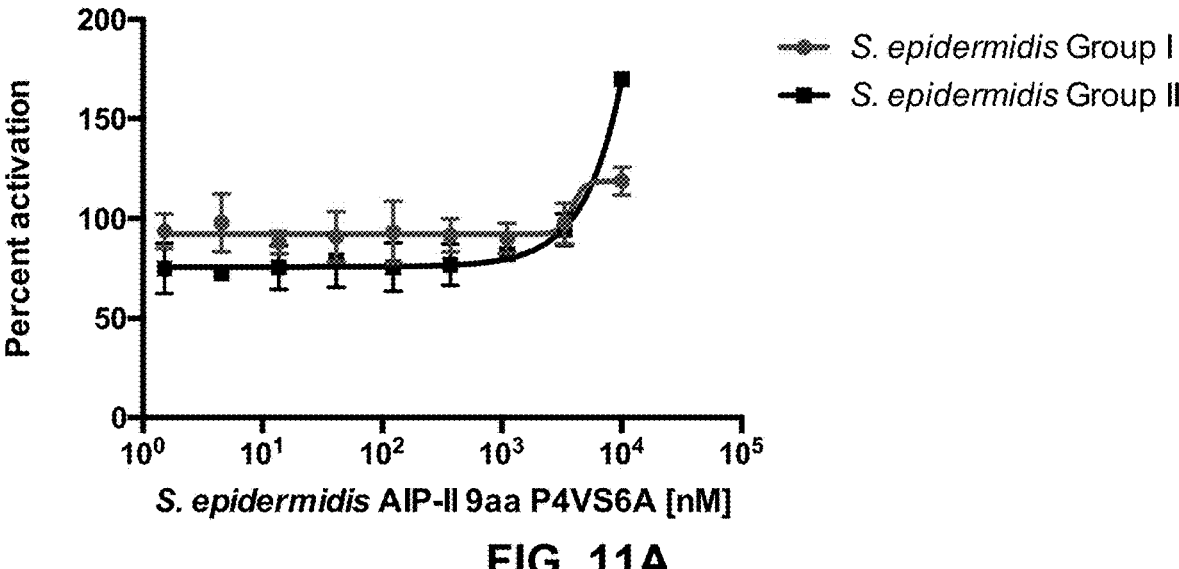
FIGS. 11A, 11B and 11C are single replicate dose response curves for antagonism or agonism as indicated.
Figure 11B:
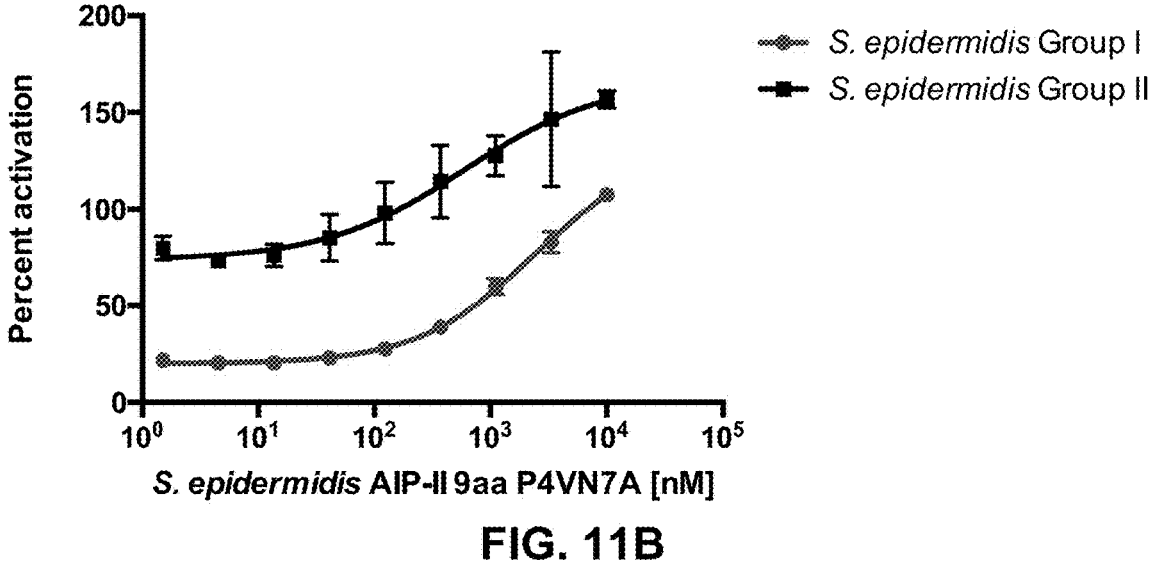
Figure 11C:
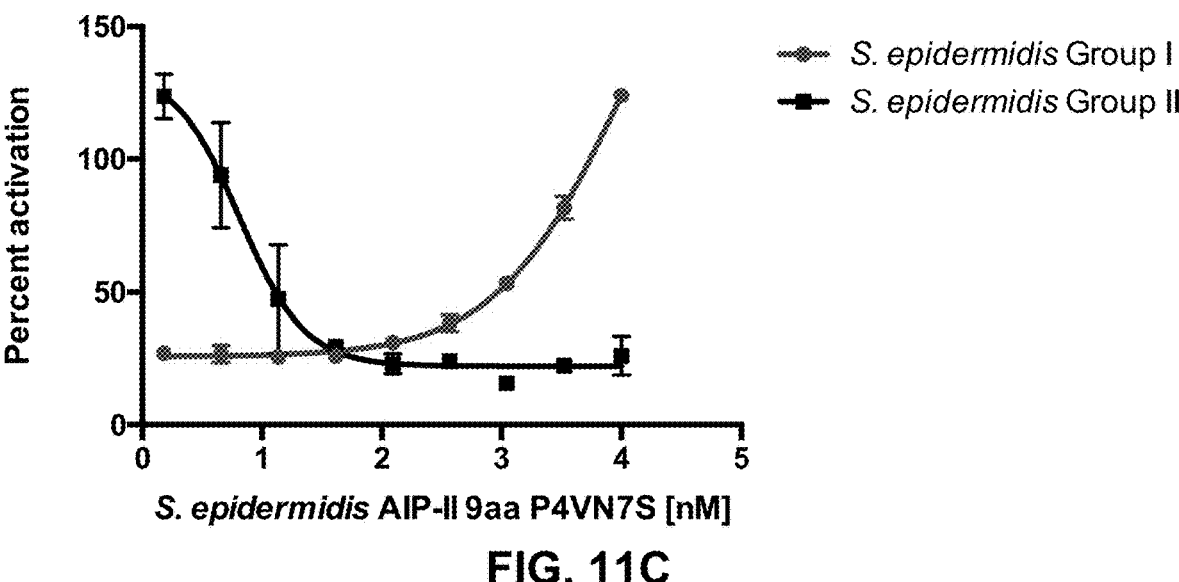

While agonists of the agr system can decrease biofilm growth, agr system antagonists are generally expected to promote biofilm accumulation. Indeed, as discussed above, this relationship between the agr system and biofilm has raised concern over the merit of inhibiting QS in *S. epidermidis* (and related staphylococcal species) as a method of reducing virulence (28, 34). To our surprise, however, exposing *S. epidermidis* Group-I to our nanomolar AgrC-I inhibitor (AIP-I D1AS6AV3AA5S) at 10 μM did not increase biofilm growth as expected in the static biofilm assay (FIG. 9). Instead, the inhibitor did not alter, and perhaps even decreased, biofilm growth. While the CV assay is a relatively rudimentary method to monitor biofilm formation and the results obtained could be specific to our experimental conditions, these results reflect the complex roles played by the agr system during biofilm formation in *S. epidermidis*. The lack of stimulation in biofilm accumulation by the antagonist is believed to be a result of the proficiency of *S. epidermidis* RP62A in PIA production, which could have maximized the formation of biofilm even in the absence of an exogenous AgrC antagonist. Inhibition of the agr system in a PIA-negative *S. epidermidis* strain could yield a more dramatic impact on biofilm formation.

Figure 6:
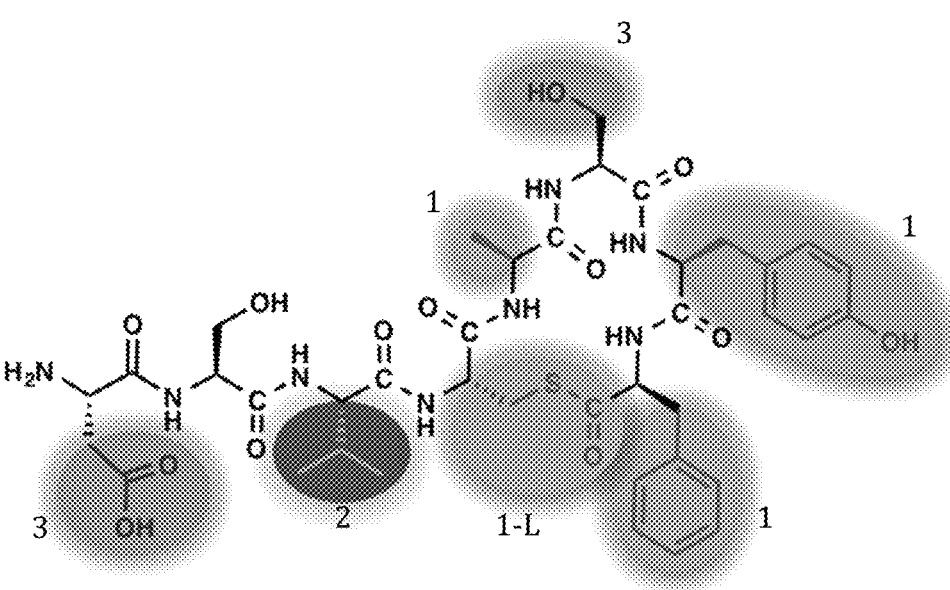
FIG. 6 illustrates a summary of the exemplary key SAR trends for activation of *S. epidermidis* AgrC-I by AIP-I as revealed by the reporter assays in this study. Red (1): important for AgrC receptor recognition. Green (2): important for AgrC receptor activation. Blue (3): detrimental to AgrC receptor activation. Remaining residues contribute, but are not key to receptor recognition. Alternative amino acid side chains of similar structure can replace the key side chains illustrated without detrimental loss of activity, see structures in the specification. Also the illustrated linker group for the macrocycle (1-L) can be replaced with —CH$_2$—NH—CO— or its N-methylated analog without detrimental loss of activity.

This work provided a series of non-native analogs of *S. epidermidis* AIP-I and performed the first systematic SAR analysis of this AIP scaffold for activation of AgrC-I (key SARs highlighted in FIG. 6). This analysis had several important outcomes. First, it revealed two hydrophobic, endocyclic residues (Tyr7 and Phe8) that, in addition to the thioester linkage and Ala5, are important for AgrC-I recognition. It was also found that the exocyclic residue Val3 is important for AgrC-I activation, and more interestingly, the Asp1 and Ser6 residues allow for submaximal activation of AgrC-I and actually could be mutated for example as descried in formulas herein to augment the agonistic potencies of AIP-I analogs.

Second, the studies revealed several highly potent, non-native AgrC modulators, including the first pan-group AgrC inhibitors for *S. epidermidis* (AIP-I D1AS6AV3A and AIP-I D1AS6AV3AA5S). A non-native agonist of AgrC-I (AIP-I D1AS6A) with improved potency over the native AIP-I was identified and it was demonstrated demonstrated that this analog was capable of strongly inhibiting *S. epidermidis* biofilm growth, an important virulence phenotype at least partially controlled by the agr system. This result indicates that the AgrC-I modulators reported herein can be used to alter QS-controlled virulence phenotypes in *S. epidermidis*. Moreover, AIP-I D1AS6A, is believed to represent the first non-native AIP analog with anti-biofilm activity in any staphylococcal species. This peptide in particular can be administered with various antibiotics for removal of *S. epidermidis* biofilm to improve the effectiveness of antibiotics.

Third, this study has provided the first set of AgrC inhibitors that, at the concentrations tested, are selective either for particular *S. epidermidis* specificity groups or for a staphylococcal species (i.e., *S. epidermidis* or *S. aureus*). These new group and species selective AgrC inhibitors now can be utilized to selectively target an agr system in a mixed bacteria population and investigate the agr interference (18, 42-44).

Yang, T. et L. (2016) "Structure-Function Analyses of a *Staphylococcus epidermidis* Autoinducing Peptide Reveals Motifs Critical for AgrC-type Receptor Modulation" ACS Chem Biol 11(7) 1882-91 reports at least a portion of the work described herein and is incorporated by reference herein in its entirety for any additional detail with respect to experiments performed.

Example 7

Peptides were designed to combine the residues found to be important for receptor activation by AIPs in Group I and Group II of *S. epidermidis*, to generate a multi-group activator (i.e., in both Groups I and II). Specifically, the valine residue from AIP-I appears to be important for activation of AgrC-I, while the final 4 amino acid residues in the exocyclic tail of AIP-II appear to be required for activation of AgrC-II. AIP-II 9aa N3L (K-Y-L-P-C-S-N-YL) (SEQ ID NO: 1) is shown be an antagonist of both *S. epidermidis* Group I and Group II, but more active in Group I (see FIG. 10A). AIP-II 9aa N3V (K-Y-V-P-C-S-N-Y-L) (SEQ ID NO: 2) is shown to be an antagonists of both *S. epidermidis* Group I and Group II, but more active in Group I (see FIG. 10B). AIP-II 9aa P4V (K-Y-N-V-C-S-N-Y-L) (SEQ ID NO: 3) is shown to be an antagonist of *S. epidermidis* Group I, yet a potent agonist of *S. epidermidis* Group II (see FIG. 1C).

Based on the activity of AIP 9aa P4V, a set of three additional analogs were designed to further explore the mutation of resides in the macrocyclic ring to generate additional multi-group activating AIP analogs. The following peptides were synthesized as described above for other AIP analogs. AIP-II 9aa P4VS6A (K-Y-N-V-C-A-N-Y-L) (SEQ ID NO: 4) is inactive toward *S. epidermidis* Group I, but has agonistic activity towards *S. epidermidis* Group II, indicating that AIP analogs can be designed that have group-specific agonistic activity with no activities toward other groups. (see FIG. 11A) A mixture of such analogs that target all receptors in *S. epidermidis* could allow for the reduction of biofilm accumulation of *S. epidermidis* without first having to identify the specific group of the strain.

AIP-II 9aa P4VN7A (K-Y-N-V-C-S-A-Y-L) (SEQ ID NO: 5) is capable of activating two different AgrC receptors in the same species, where the native AIPs of those receptors are antagonistic toward each other. (see FIG. 11B) This is an unexpected finding.

While AIP-II 9aa P4V is found to be an agonist for *S. epidermidis* Group II, and an antagonist for *S. epidermidis* Group I, the activities toward *S. epidermidis* Group I and II are switched with the introduction of an asparagine to serine substitution in the macrocyclic ring, for example in AIP-II 9aa P4VN7S (K-Y-N-V-C-S-S-Y-L) (SEQ ID NO: 6). (see FIG. 11C) This observation indicates that this endocyclic position plays a role in the mode of activity toward AgrC-I and AgrC-II. Table 3 provides estimated $EC_{50}$ and $IC_{50}$ values for indicated receptors for compounds of this example.

TABLE 3

| Estimated $EC_{50}$ and $IC_{50}$ values for compounds of Example 7 in *S. epidermidis* | | | | |
|---|---|---|---|---|
| Peptides | AgrC-I: $EC_{50}$ | AgrC-I: $IC_{50}$ | AgrC-II: $EC_{50}$ | AgrC-II: $IC_{50}$ |
| AIP-II 9aa N3L | — | 9.4 nM | — | 70.7 nM |
| AIP-II 9aa N3V | — | 4.1 nM | — | 107.7 nM |
| AIP-II 9aa P4V | — | 45.0 nM | 113.8 nM | — |
| AIP-II 9aa P4V S6A | — | — | >7000 nM | — |
| AIP-II 9aa P4V N7A | >1200 nM | — | >600 nM | — |
| AIP-II 9aa P4V N7S | >1800 nM | — | — | 6.5 nM |

Example 8

Methods

Biological reagents, strains, and general methods. All standard reagents were purchased from commercial sources and used according to enclosed instructions. The *S. epidermidis* fluorescence reporter strains AH3408 (Group-I), AH3567 (Group-II), and AH3409 (Group-III) were cultured in Tryptic Soy Broth (TSB, from Sigma) augmented with 10

µg/mL of erythromycin (36). The *S. epidermidis* wild-type strain RP62A (Group-I) was cultured in TSB (from Sigma or EMD Millipore). The *S. aureus* fluorescence reporter strains AH1677 (Group-I), AH430 (Group-II), AH1747 (Group-III), and AH1872 (Group-IV) were cultured in Brain Heart Infusion (BHI, from Teknova) augmented with 10 µg/mL of chloramphenicol (65). All cultures were grown at 37° C. with shaking (200 rpm) unless noted otherwise. Absorbance and fluorescence measurements were obtained using a Biotek Synergy 2 microplate reader operating Gen5 data analysis software. $IC_{50}$ values and $EC_{50}$ values were determined from sigmoidal curve fits using GraphPad Prism software (v. 6.0).

Peptide synthesis. *S. epidermidis* AIP analogs were synthesized on solid-phase resin, purified by preparative high performance liquid chromatography (HPLC), and characterized using our previously reported methods (59). See Supplementary Information for mass spectrometry (MS) and HPLC characterization data for the peptides in this study, as well as additional information on reagents and instrumentation used in peptide synthesis.

Fluorescence reporter assay protocol. For AgrC antagonism assays, peptide stock solutions in DMSO (1 mM) were serially diluted with DMSO (either 1:3 or 1:10), and 2 µL aliquots of the diluted solutions were added to each of the wells in a black 96-well polystyrene microtiter plate (Costar). Each peptide solution was tested in triplicate. As a negative control, 2 µL of DMSO was included. An overnight culture of the *S. epidermidis* or *S. aureus* fluorescence reporter strain was diluted 1:50 with fresh media, and 198 µL of the diluted culture were added to each of the wells of the microtiter plate containing peptide. Plates were then incubated at 37° C. for 24 h. Fluorescence (EX 500 nm/EM 540 nm) and $OD_{600}$ of each well was measured using a plate reader, and the fluorescence values were normalized to the DMSO control. For *S. epidermidis* AgrC-I agonism assays, an additional 2 µL of *S. epidermidis* AIP-II stock solution was added to the wells to a final concentration of 50 nM, in order to block AgrC-I activation by endogenously produced AIP-I. The remaining steps of the fluorescence assay were the same as above.

For single-concentration fluorescence reporter assays, 2 µL of the peptide stock solutions were added to the wells in a black 96-well microtiter plate to a final concentration of 10 µM, 1 µM, or 100 nM. The remaining steps of the fluorescence assay were the same as above.

Crystal violet biofilm assay protocol. Peptide stock solutions were serially diluted with DMSO (1:3), and 2 µL of the diluted solutions were added to each of the wells in a clear, flat-bottom, 96-well polystyrene microtiter plate (Costar). Each solution was tested in triplicate. As a negative control, 2 µL of DMSO was included. An overnight culture of *S. epidermidis* RP62A was diluted 1:100 with fresh TSB (EMD Millipore) augmented with 0.5% glucose, and 198 µL of the diluted culture were added to each of the wells of the microtiter plate containing peptides. Bacteria were incubated at 37° C. for 24 h under static conditions. Quantification of the amount of biofilm formed using crystal violet (CV) assays was performed according to previously reported protocols (66). For single-concentration CV assays, 2 µL of the peptide stock solutions were added to the wells to a final concentration of 10 µM. The remaining steps of the biofilm assay were the same as above.

REFERENCES

1. Vuong, C., and Otto, M. (2002) *Staphylococcus epidermidis* infections, *Microb. Infect.* 4, 481-489.

2. von Eiff, C., Peters, G., and Heilmann, C. (2002) Pathogenesis of infections due to coagulase-negative staphylococci, *Lancet Infect. Dis.* 2, 677-685.

3. Otto, M. (2009) *Staphylococcus epidermidis*—the 'accidental' pathogen, *Nat. Rev. Microbiol.* 7, 555-567.

4. McCann, M. T., Gilmore, B. F., and Gorman, S. P. (2008) *Staphylococcus epidermidis* device-related infections: pathogenesis and clinical management, *J. Pharm. Pharmacol.* 60, 1551-1571.

5. Mertens, A., and Ghebremedhin, B. (2013) Genetic determinants and biofilm formation of clinical *Staphylococcus epidermidis* isolates from blood cultures and indwelling devises, *Eur. J. Microbiol. Immunol.* (*Bp*) 3, 111-119.

6. Rogers, K. L., Fey, P. D., and Rupp, M. E. (2009) Coagulase-negative staphylococcal infections, *Infect. Dis. Clin. North Am.* 23, 73-98.

7. Costerton, J. W., Stewart, P. S., and Greenberg, E. P. (1999) Bacterial biofilms: a common cause of persistent infections, *Science* 284, 1318-1322.

8. Claessens, J., Roriz, M., Merckx, R., Baatsen, P., Van Mellaert, L., and Van Eldere, J. (2015) Inefficacy of vancomycin and teicoplanin in eradicating and killing *Staphylococcus epidermidis* biofilms in vitro, *Int. J. Antimicrob. Agents* 45, 368-375.

9. Cheung, G. Y., Joo, H. S., Chatterjee, S. S., and Otto, M. (2014) Phenol-soluble modulins—critical determinants of staphylococcal virulence, *FEMS Microbiol. Rev.* 38, 698-719.

10. Kong, K. F., Vuong, C., and Otto, M. (2006) *Staphylococcus* quorum sensing in biofilm formation and infection, *Int. J. Med. Microbiol.* 296, 133-139.

11. Vuong, C., Durr, M., Carmody, A. B., Peschel, A., Klebanoff, S. J., and Otto, M. (2004) Regulated expression of pathogen-associated molecular pattern molecules in *Staphylococcus epidermidis:* quorum-sensing determines pro-inflammatory capacity and production of phenol-soluble modulins, *Cell. Microbiol.* 6, 753-759.

12. Wang, C., Li, M., Dong, D., Wang, J., Ren, J., Otto, M., and Gao, Q. (2007) Role of ClpP in biofilm formation and virulence of *Staphylococcus epidermidis, Microb. Infect.* 9, 1376-1383.

13. Yao, Y., Vuong, C., Kocianova, S., Villaruz, A. E., Lai, Y., Sturdevant, D. E., and Otto, M. (2006) Characterization of the *Staphylococcus epidermidis* accessory-gene regulator response: quorum-sensing regulation of resistance to human innate host defense, *J. Infect. Dis.* 193, 841-848.

14. Camilli, A., and Bassler, B. L. (2006) Bacterial small-molecule signaling pathways, *Science* 311, 1113-1116.

15. Rutherford, S. T., and Bassler, B. L. (2012) Bacterial quorum sensing: its role in virulence and possibilities for its control, *Cold Spring Harb. Perspect. Med.* 2, a012427.

16. Lyon, G. J., and Novick, R. P. (2004) Peptide signaling in *Staphylococcus aureus* and other Gram-positive bacteria, *Peptides* 25, 1389-1403.

17. Novick, R. P., and Geisinger, E. (2008) Quorum sensing in staphylococci, *Annu. Rev. Genet.* 42, 541-564.

18. Thoendel, M., Kavanaugh, J. S., Flack, C. E., and Horswill, A. R. (2011) Peptide signaling in the staphylococci, *Chem. Rev.* 111, 117-151.

19. George, E. A., and Muir, T. W. (2007) Molecular mechanisms of agr quorum sensing in virulent staphylococci, *ChemBioChem* 8, 847-855.

20. Ji, G., Beavis, R. C., and Novick, R. P. (1995) Cell density control of staphylococcal virulence mediated by an octapeptide pheromone, *Proc. Natl. Acad. Sci. USA* 92, 12055-12059.

21. Kavanaugh, J. S., Thoendel, M., and Horswill, A. R. (2007) A role for type I signal peptidase in *Staphylococcus aureus* quorum sensing, *Mol. Microbiol.* 65, 780-798.

22. Wang, B., Zhao, A., Novick, R. P., and Muir, T. W. (2014) Activation and inhibition of the receptor histidine kinase AgrC occurs through opposite helical transduction motions, *Mol. Cell* 53, 929-940.

23. George Cisar, E. A., Geisinger, E., Muir, T. W., and Novick, R. P. (2009) Symmetric signalling within asymmetric dimers of the *Staphylococcus aureus* receptor histidine kinase AgrC, *Mol. Microbiol.* 74, 44-57.

24. Novick, R. P., Ross, H. F., Projan, S. J., Kornblum, J., Kreiswirth, B., and Moghazeh,
S. (1993) Synthesis of staphylococcal virulence factors is controlled by a regulatory RNA molecule, *EMBO J.* 12, 3967-3975.

25. Otto, M. (2014) Phenol-soluble modulins, *Int. J. Med. Microbiol.* 304, 164-169.

26. Buttner, H., Mack, D., and Rohde, H. (2015) Structural basis of *Staphylococcus epidermidis* biofilm formation: mechanisms and molecular interactions, *Front. Cell. Infect. Microbiol.* 5, 14.

27. Otto, M. (2004) Virulence factors of the coagulase-negative staphylococci, *Front.*
Biosci. 9, 841-863.

28. Mack, D., Davies, A. P., Harris, L. G., Rohde, H., Horstkotte, M. A., and Knobloch, J.
K. (2007) Microbial interactions in *Staphylococcus epidermidis* biofilms, *Anal. Bioanal. Chem.* 387, 399-408.

29. Vuong, C., Gerke, C., Somerville, G. A., Fischer, E. R., and Otto, M. (2003) Quorum-sensing control of biofilm factors in *Staphylococcus epidermidis, J. Infect. Dis.* 188, 706-718.

30. Wang, R., Khan, B. A., Cheung, G. Y., Bach, T. H., Jameson-Lee, M., Kong, K. F., Queck, S. Y., and Otto, M. (2011) *Staphylococcus epidermidis* surfactant peptides promote biofilm maturation and dissemination of biofilm-associated infection in mice, *J. Clin. Invest.* 121, 238-248.

31. Le, K. Y., Dastgheyb, S., Ho, T. V., and Otto, M. (2014) Molecular determinants of staphylococcal biofilm dispersal and structuring, *Front. Cell. Infect. Microbiol.* 4, 167.

32. Boles, B. R., and Horswill, A. R. (2008) agr-mediated dispersal of *Staphylococcus aureus* biofilms, *PLoS Path.* 4, e1000052.

33. Vuong, C., Kocianova, S., Yao, Y., Carmody, A. B., and Otto, M. (2004) Increased colonization of indwelling medical devices by quorum-sensing mutants of *Staphylococcus epidermidis* in vivo, *J. Infect. Dis.* 190, 1498-1505.

34. Otto, M. (2004) Quorum-sensing control in Staphylococci—a target for antimicrobial drug therapy?, *FEMS Microbiol. Lett.* 241, 135-141.

35. Otto, M. (2013) Staphylococcal infections: mechanisms of biofilm maturation and detachment as critical determinants of pathogenicity, *Annu. Rev. Med.* 64, 175-188.

36. Olson, M. E., Todd, D. A., Schaeffer, C. R., Paharik, A. E., Van Dyke, M. J., Buttner, H., Dunman, P. M., Rohde, H., Cech, N. B., Fey, P. D., and Horswill, A. R. (2014) *Staphylococcus epidermidis* agr quorum-sensing system: signal identification, cross talk, and importance in colonization, *J. Bacteriol.* 196, 3482-3493.

37. Klug, D., Wallet, F., Kacet, S., and Courcol, R. J. (2003) Involvement of adherence and adhesion *Staphylococcus epidermidis* genes in pacemaker lead-associated infections, *J. Clin. Microbiol.* 41, 3348-3350.

38. Hellmark, B., Soderquist, B., Unemo, M., and Nilsdotter-Augustinsson, A. (2013) Comparison of *Staphylococcus epidermidis* isolated from prosthetic joint infections and commensal isolates in regard to antibiotic susceptibility, agr type, biofilm production, and epidemiology, *Int. J. Med. Microbiol.* 303, 32-39.

39. Lianhua, Y., Yunchao, H., Guangqiang, Z., Kun, Y., Xing, L., and Fengli, G. (2014) The effect of iatrogenic *Staphylococcus epidermidis* intercellar adhesion operon on the formation of bacterial biofilm on polyvinyl chloride surfaces, *Surg. Infect. (Larchmt)* 15, 768-773.

40. Schaeffer, C. R., Woods, K. M., Longo, G. M., Kiedrowski, M. R., Paharik, A. E., Buttner, H., Christner, M., Boissy, R. J., Horswill, A. R., Rohde, H., and Fey, P. D. (2015) Accumulation-associated protein enhances *Staphylococcus epidermidis* biofilm formation under dynamic conditions and is required for infection in a rat catheter model, *Infect. Immun.* 83, 214-226.

41. Carmody, A. B., and Otto, M. (2004) Specificity grouping of the accessory gene regulator quorum-sensing system of *Staphylococcus epidermidis* is linked to infection, *Arch. Microbiol.* 181, 250-253.

42. Ji, G., Beavis, R., and Novick, R. P. (1997) Bacterial interference caused by autoinducing peptide variants, *Science* 276, 2027-2030.

43. Mayville, P., Ji, G., Beavis, R., Yang, H., Goger, M., Novick, R. P., and Muir, T. W. (1999) Structure-activity analysis of synthetic autoinducing thiolactone peptides from *Staphylococcus aureus* responsible for virulence, *Proc. Natl. Acad. Sci. USA* 96, 1218-1223.

44. Wright, J. S., 3rd, Jin, R., and Novick, R. P. (2005) Transient interference with staphylococcal quorum sensing blocks abscess formation, *Proc. Natl. Acad. Sci. USA* 102, 1691-1696.

45. Otto, M. (2001) *Staphylococcus aureus* and *Staphylococcus epidermidis* peptide pheromones produced by the accessory gene regulator agr system, *Peptides* 22, 1603-1608.

46. Otto, M., Echner, H., Voelter, W., and Gotz, F. (2001) Pheromone cross-inhibition between *Staphylococcus aureus* and *Staphylococcus epidermidis, Infect. Immun.* 69, 1957-1960.

47. Otto, M., Sussmuth, R., Vuong, C., Jung, G., and Gotz, F. (1999) Inhibition of virulence factor expression in *Staphylococcus aureus* by the *Staphylococcus epidermidis* agr pheromone and derivatives, *FEBS Lett.* 450, 257-262.

48. Fleming, V., Feil, E., Sewell, A. K., Day, N., Buckling, A., and Massey, R. C. (2006) Agr interference between clinical *Staphylococcus aureus* strains in an insect model of virulence, *J. Bacteriol.* 188, 7686-7688.

49. Lina, G., Boutite, F., Tristan, A., Bes, M., Etienne, J., and Vandenesch, F. (2003) Bacterial Competition for Human Nasal Cavity Colonization: Role of Staphylococcal agr Alleles, *Appl. Environ. Microbiol.* 69, 18-23.

50. Amara, N., Krom, B. P., Kaufmann, G. F., and Meijler, M. M. (2011) Macromolecular inhibition of quorum sensing: enzymes, antibodies, and beyond, *Chem. Rev.* 111, 195-208.

51. Galloway, W. R., Hodgkinson, J. T., Bowden, S., Welch, M., and Spring, D. R. (2012)
Applications of small molecule activators and inhibitors of quorum sensing in Gram-negative bacteria, *Trends Microbiol.* 20, 449-458.

52. Praneenararat, T., Palmer, A. G., and Blackwell, H. E. (2012) Chemical methods to interrogate bacterial quorum sensing pathways, *Org. Biomol. Chem.* 10, 8189-8199.

53. P., M., Affas, Z., Reynolds, C., Holden, M. T., Wood, S. J., Saint, S., Cockayne, A., Hill, P. J., Dodd, C. E., Bycroft, B. W., Chan, W. C., and Williams, P. (2001) Structure, activity and evolution of the group I thiolactone peptide quorum-sensing system of *Staphylococcus aureus*, Mol. Microbiol. 41, 503-512.

54. Lyon, G. J., Mayville, P., Muir, T. W., and Novick, R. P. (2000) Rational design of a global inhibitor of the virulence response in *Staphylococcus aureus*, based in part on localization of the site of inhibition to the receptor-histidine kinase, AgrC, *Proc. Natl. Acad. Sci. USA* 97, 13330-13335.

55. Lyon, G. J., Wright, J. S., Muir, T. W., and Novick, R. P. (2002) Key determinants of receptor activation in the agr autoinducing peptides of *Staphylococcus aureus, Biochemistry* 41, 10095-10104.

56. Scott, R. J., Lian, L. Y., Muharram, S. H., Cockayne, A., Wood, S. J., Bycroft, B. W., Williams, P., and Chan, W. C. (2003) Side-chain-to-tail thiolactone peptide inhibitors of the staphylococcal quorum-sensing system, *Bioorg. Med. Chem. Lett.* 13, 2449-2453.

57. George, E. A., Novick, R. P., and Muir, T. W. (2008) Cyclic peptide inhibitors of staphylococcal virulence prepared by Fmoc-based thiolactone peptide synthesis, *J. Am. Chem. Soc.* 130, 4914-4924.

58. Fowler, S. A., Stacy, D. M., and Blackwell, H. E. (2008) Design and synthesis of macrocyclic peptomers as mimics of a quorum sensing signal from *Staphylococcus aureus, Org. Lett.* 10, 2329-2332.

59. Tal-Gan, Y., Stacy, D. M., Foegen, M. K., Koenig, D. W., and Blackwell, H. E. (2013) Highly potent inhibitors of quorum sensing in *Staphylococcus aureus* revealed through a systematic synthetic study of the group-III autoinducing peptide, *J. Am. Chem. Soc.* 135, 7869-7882.

60. Tal-Gan, Y., Stacy, D. M., and Blackwell, H. E. (2014) N-Methyl and peptoid scans of an autoinducing peptide reveal new structural features required for inhibition and activation of AgrC quorum sensing receptors in *Staphylococcus aureus, Chem. Commun. (Camb.)* 50, 3000-3003.

61. Johnson, J. G., Wang, B., Debelouchina, G. T., Novick, R. P., and Muir, T. W. (2015) Increasing AIP Macrocycle Size Reveals Key Features of agr *Activation in Staphylococcus aureus, ChemBioChem* 16, 1093-1100.

62. Otto, M., Sussmuth, R., Jung, G., and Gotz, F. (1998) Structure of the pheromone peptide of the *Staphylococcus epidermidis* agr system, *FEBS Lett.* 424, 89-94.

63. Khan, B. A., Yeh, A. J., Cheung, G. Y., and Otto, M. (2015) Investigational therapies targeting quorum-sensing for the treatment of *Staphylococcus aureus* infections, *Expert Opin. Investig. Drugs* 24, 689-704.

64. Tal-Gan, Y., Ivancic, M., Cornilescu, G., Cornilescu, C. C., and Blackwell, H. E. (2013) Structural characterization of native autoinducing peptides and abiotic analogues reveals key features essential for activation and inhibition of an AgrC quorum sensing receptor in *Staphylococcus aureus, J. Am. Chem. Soc.* 135, 18436-18444.

65. Kirchdoerfer, R. N., Garner, A. L., Flack, C. E., Mee, J. M., Horswill, A. R., Janda, K. D., Kaufmann, G. F., and Wilson, I. A. (2011) Structural basis for ligand recognition and discrimination of a quorum-quenching antibody, *J. Biol. Chem.* 286, 17351-17358.

66. Kratochvil, M. J., Tal-Gan, Y., Yang, T., Blackwell, H. E., and Lynn, D. M. (2015) Nanoporous Superhydrophobic Coatings that Promote the Extended Release of Water-Labile Quorum Sensing Inhibitors and Enable Long-Term Modulation of Quorum Sensing in *Staphylococcus aureus, ACS Biomater. Sci. Eng.* 1, 1039-1049.

We claim:

1. A compound which is selected from the peptides of:

```
                              (SEQ ID NO: 176)
K-Y-L-P-(C-S-N-Y-L), (SEQ ID NO: 177)
K-Y-V-P-(C-S-N-Y-L), (SEQ ID NO: 178)
K-Y-N-V-(C-S-N-Y-L), (SEQ ID NO: 179)
K-Y-N-V-(C-A-N-Y-L), (SEQ ID NO: 180)
K-Y-N-V-(C-S-A-Y-L), (SEQ ID NO: 181)
K-Y-N-V-(C-S-S-Y-L), (SEQ ID NO: 94)
A-S-A-(C-A-A-Y-F), (SEQ ID NO: 95)
A-S-A-(C-S-A-Y-F)
``` or salts of any thereof.

2. A method for modulating quorum sensing in *S. epidermidis* which comprises contacting the bacterium or an environment containing the bacterium with one or more compounds or salts of claim 1.

3. A method for inhibiting an AgrC receptor of *S. epidermidis* or *S. aureus* which comprises contacting the bacterium or an environment containing the bacterium with one or more compounds or salts of claim 1.

4. A pharmaceutical composition for treating *Staphylococcus* infection which comprises one or more compounds or salts of claim 1.

5. The compound of claim 1 which is the peptide:

```
                              (SEQ ID NO: 176)
K-Y-L-P-(C-S-N-Y-L), (SEQ ID NO: 94)
A-S-A-(C-A-A-Y-F),
or (SEQ ID NO: 95)
A-S-A-(C-S-A-Y-F).
```

* * * * *